US006984634B2

(12) United States Patent
Cundy et al.

(10) Patent No.: US 6,984,634 B2
(45) Date of Patent: Jan. 10, 2006

(54) BILE-ACID CONJUGATES FOR PROVIDING SUSTAINED SYSTEMIC CONCENTRATIONS OF DRUGS

(75) Inventors: Kenneth C. Cundy, Redwood City, CA (US); Mark A. Gallop, Los Altos, CA (US)

(73) Assignee: XenoPort, Inc., Santa Clara, CA (US)

( * ) Notice: Subject to any disclaimer, the term of this patent is extended or adjusted under 35 U.S.C. 154(b) by 114 days.

(21) Appl. No.: 09/974,768

(22) Filed: Oct. 9, 2001

(65) Prior Publication Data

US 2002/0142998 A1 Oct. 3, 2002

Related U.S. Application Data

(60) Provisional application No. 60/238,758, filed on Oct. 6, 2000, provisional application No. 60/249,804, filed on Nov. 17, 2000, and provisional application No. 60/297,472, filed on Jun. 11, 2001.

(51) Int. Cl.
*A61K 31/58* (2006.01)
*A61K 31/56* (2006.01)
*C07J 9/00* (2006.01)
*C07J 43/00* (2006.01)

(52) U.S. Cl. .................. 514/172; 514/182; 540/107; 540/108; 552/549; 552/551

(58) Field of Classification Search .............. 514/172, 514/182; 540/108, 107; 552/549, 551
See application file for complete search history.

(56) References Cited

U.S. PATENT DOCUMENTS

| 3,326,758 | A | 6/1967 | Irmscher et al. |
| 4,560,512 | A | 12/1985 | Firestone |
| 5,352,682 | A | 10/1994 | Sipos |
| 5,462,933 | A | 10/1995 | Kramer et al. |
| 5,541,348 | A | 7/1996 | Ayra et al. |
| 5,646,272 | A | 7/1997 | Kramer et al. |
| 5,668,126 | A | 9/1997 | Kramer et al. |
| 5,695,738 | A | 12/1997 | Anderson et al. |
| 5,725,840 | A | 3/1998 | Klaveness et al. |
| 5,942,248 | A | 8/1999 | Barnwell |
| 6,143,738 | A | 11/2000 | Zasloff |
| 6,288,041 | B1 | 9/2001 | Chaki et al. |

FOREIGN PATENT DOCUMENTS

| EP | 0272462 B1 | | 6/1988 |
| JP | 11-60594 | * | 3/1999 |
| JP | 11-60954 | | 3/1999 |
| WO | WO 01/76531 A2 | | 10/2001 |
| WO | WO 02/100347 A2 | | 12/2002 |

OTHER PUBLICATIONS

Database esp@cenet on STN, PN KR9701149 (Kim Young–Man et al.), Jan. 29, 1997, Abstract only.
Swaan et al., Preface. Advanced Drug Delivery Reviews. 1996, vol. 20, pp. 1–3, see entire document.
Russell–Jones et al., "Vitamin B12 Mediated Oral Delivery Systems for Granulocyte–Colony Stimulating Factor and Erythropoietin," *Bioconjugate Chemistry*, 1995, vol. 6, pp. 459–465, see entire document.
Shah et al., "Transcellular Delivery of an Insulin–Transferrin Conjugate in Enterocyte–like Caco–2 Cells," *J. of Pharm. Sci.*, Dec. 1996, vol. 85, No. 12, pp. 1306–1311, see entire document.
Swaan et al., "Use of intestinal and hepatic bile acid transporters for drug delivery," *Advanced Drug Delivery Reviews*, 1996, vol. 20, pp. 59–82, see especially pp. 75 and 76.
Kagedahl et al., "Use of the Intestinal Bile Acid Transporter for the Uptake of Cholic Acid Conjugates with HIV–1 Protease Inhibitory Activity," *Pharm. Res.*, 1997, vol. 14, No. 2, pp. 176–180, see entire document.
International Search Report mailed Jan. 22, 2002 from PCT/US01/42513.
International Search Report mailed Jan. 23, 2002 from PCT/US01/31486.
International Search Report mailed Dec. 31, 2001 from PCT/US01/31394.
Adibi, S.A., "The oligopeptide transporter (Pept–1) in human intestine: Biology and Function", *Gastroenterology*, vol. 113, pp. 332–340, 1997.
Baringhaus, K.H., et al., "Substrate specificity of the ileal and hepatic $Na^+$ / bile acid cotransporters of the rabbit. II. A reliable 3D QSAR pharmacophore model for the ileal $Na^+$ / bile acid cotransporter", *J. Lipid Res.*, vol. 40, pp. 2158–2168, 1999.
Bryans, J. S., et al., "3–Substituted GABA analogs with central nervous system activity: a review", *Med. Res. Rev.*, vol. 19, pp. 149–177, 1999.
Bundgaard, H., in *Design of Prodrugs* (Bundgaard, H. Ed.), Elsevier Science B.V., pp. 1–92, 1985.
Dieck, S.T., et al., "The peptide transporter PepT2 is expressed in rat brain and mediates the accumulation of the fluorescent dipeptide derivative $\beta$–Ala–Lys–$N_E$–AMCA in astrocytes", *GLIA*, vol., 25, pp. 10–20, 1999.
Ho, N. F. H., "Utilizing bile acid carrier mechanisms to enhance liver and small intestine absorption", *Ann. N. Y. Acad. Sci.*, vol. 507, pp. 315–329, 1987.

(Continued)

*Primary Examiner*—Barbara P. Badio
(74) *Attorney, Agent, or Firm*—Buchanan Ingersoll PC

(57) ABSTRACT

This invention is directed to compounds that provide for sustained systemic concentrations of therapeutic or prophylactic agents following administration to animals. This invention is also directed to pharmaceutical compositions including and methods using such compounds.

5 Claims, 5 Drawing Sheets

OTHER PUBLICATIONS

Jezyk, N., et al., "Transport of Pregabalin in Rat Intestine and Caco–2 Monolayers", *Pharm. Res.*, vol. 16, pp. 519–526, 1999.

Kagedahl, M., et al., "Use of the intestinal bile acid transporter for the uptake of cholic acid conjugates with HIV–1 protease inhibitory activity", *Pharm. Res.*, vol. 14, pp. 176–180, 1997.

Kim, D.C., "Evaluation of bile acid transporter in enhancing intestinal permeability of renin–inhibitory peptides", *J. Drug Targeting*, vol. 1, pp. 347–359, 1993.

Kramer, W, et al., "Liver–specific drug targeting by coupling to bile acids", *J. Biol. Chem.*, vol. 267, pp. 18598–18604, 1992.

Kramer, W., et al., "Intestinal absorption of peptides by coupling to bile acids", *J. Biol. Chem.*, vol. 269, pp. 10621–10627, 1994.

Kramer, W., "Bile acid derived HMG–CoA reductase inhibitors", *Biochim. Biophys. Acta.*, vol. 1227, pp. 137–154, 1994.

Kramer, W., et al., "Substrate specificity of the ileal and hepatic $Na^+$ / bile acid cotransporters of the rabbit. I. Transport studies with membrane vesicles and cell lines expressing the cloned transporters", *J. Lipid Res.*, vol. 40, pp. 1604–1617, 1999.

Kullak–Ublick, G.A., et al., "Hepatobiliary transport", *J. Hepatology*, vol. 32 (*Suppl. 1*), pp. 3–18, 2000.

Leibach, et al., "Peptide transporters in the intestine and the kidney", *Ann. Rev. Nutr.*, vol. 16, pp. 99–119, 1996.

Mills, C.O., et al., "Ileal absorption of tyrosine–conjugated bile acids in Wistar rats", *Biochim. Biophys. Acta*, vol. 926, pp. 154–159, 1987.

Navia, M.A, "Design principles for orally bioavailable drugs", *Drug Discovery Today*, vol. 1, pp. 179–189, 1996.

Petzinger, E., et al., "Hepatobiliary transport of hepatic 3–hydroxy–3–methylglutaryl coenzyme A reductase inhibitors conjugated with bile acids", *Hepatology*, vol. 22, pp. 1801–1811, 1995.

Swaan, P.W., *Use of the intestinal and hepatic bile acid transporters for drug delivery*, Adv. Drug Delivery Rev, 1996, 20, pp. 59–82.

Swaan, P.W., et al., "Enhanced transepithelial transport of peptides by conjugation to cholic acid", *Bioconj. Chem*, vol. 8, pp. 520–525, 1997.

Tsuji, A., et al., "Carrier–mediated intestinal transport of drugs", *Pharm. Res.*, vol. 13, pp. 963–977, 1996.

Wong, et al., "Electrophysiological characteristics of the proton–coupled peptide transporter PEPT2 cloned from rat brain", *Am. J. Physiol.*, vol. 275, pp. C967–C975, 1998.

Wess, G., et al., "Synthesis of Bile Acid –Drug Conjugates: Potential Drug–Shuttles for Liver Specific Targeting", *Tetrahedron Letters*34(5):819–822 (1993).

Wess, G., et al., Preparation of 3α–and 3β–ω–Aminoalkoxy)–7 α, 12α–Dihydroxy–5β–Cholanioic Acid Esters: Versatile Shuttles for Drug Targeting, *Tetrahedron Letters*34(5):817 (1993).

European Search Report from EP01 97 8853 dated May 25, 2005.

\* cited by examiner

*The Enterohepatic Circulation with Key Transporter Proteins Mediating Bile Acid Circulation*

Bile Acid Conjugates of HMG-CoA Reductase Inhibitor

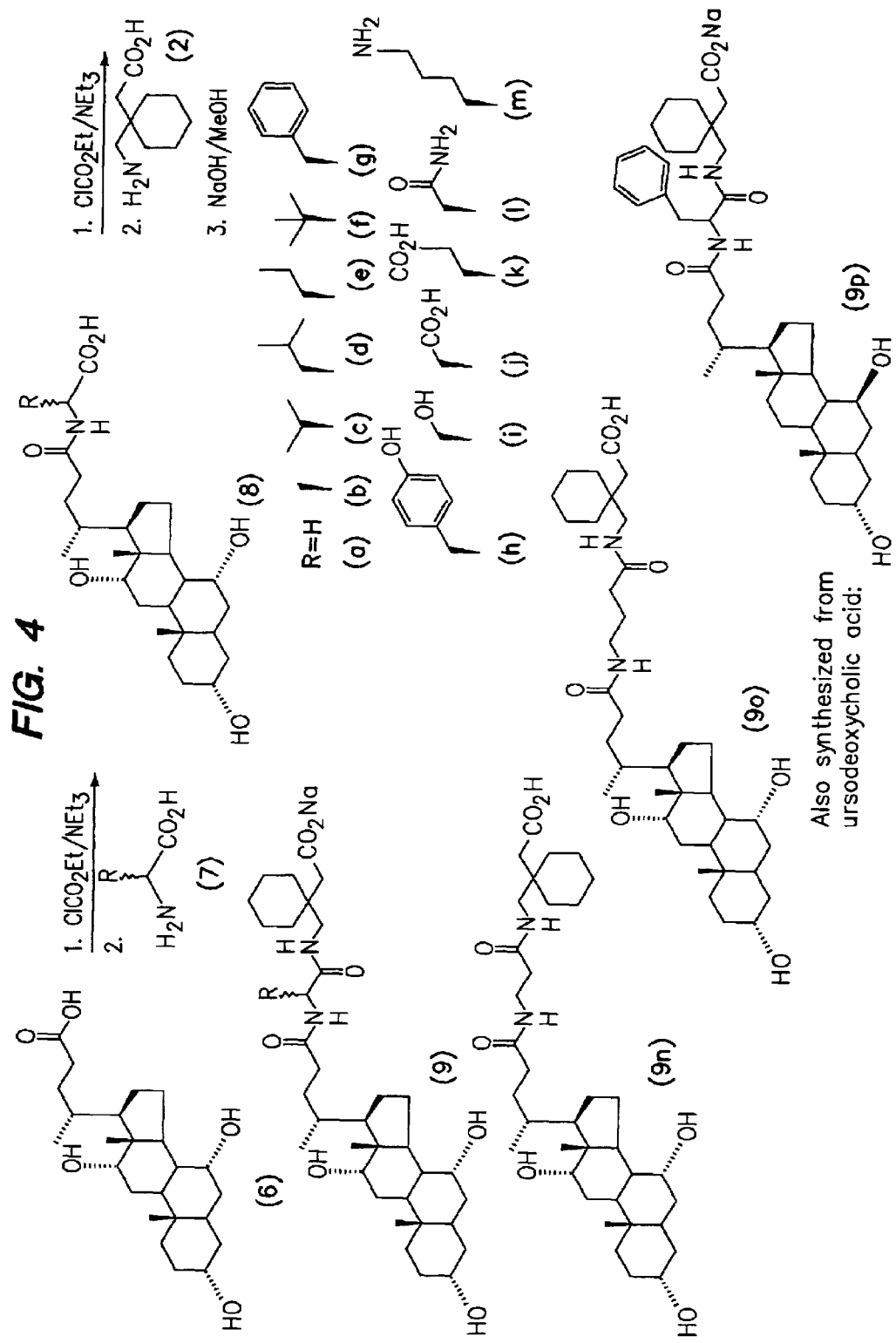

FIG. 7
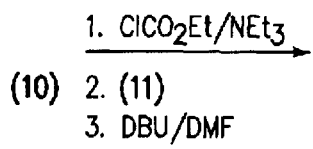
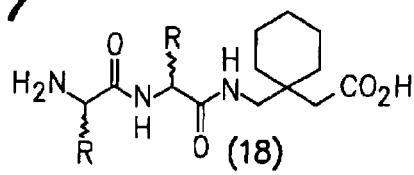
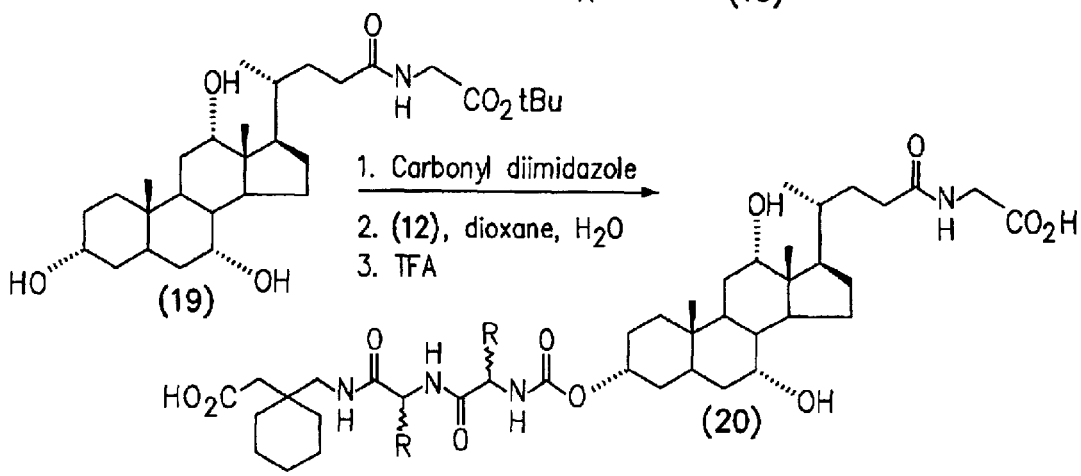
FIG. 8
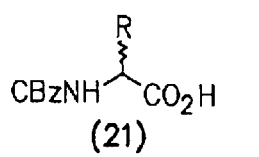
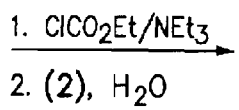
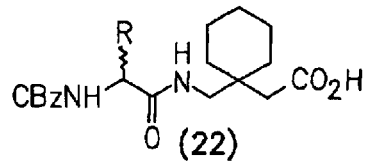
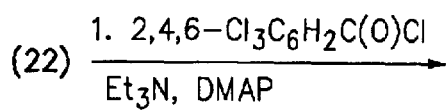
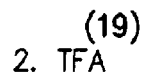
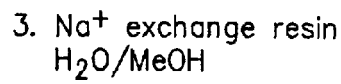
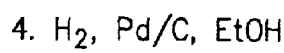
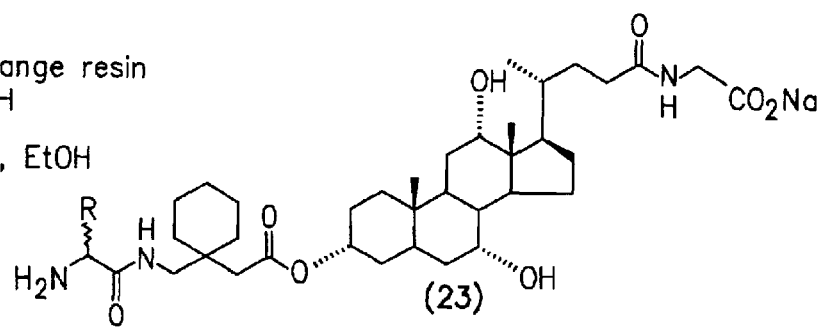

BILE-ACID CONJUGATES FOR PROVIDING SUSTAINED SYSTEMIC CONCENTRATIONS OF DRUGS

CROSS REFERENCE TO RELATED APPLICATIONS

This application claims the benefit of U.S. Provisional Application Ser. Nos. 60/238,758, filed Oct. 6, 2000, 60/249,804, filed Nov. 17, 2000, and 60/297,472, filed Jun. 11, 2001, all of which are incorporated by reference in their entirety.

BACKGROUND OF THE INVENTION

1. Field of the Invention

This invention is directed to compounds that provide for sustained systemic concentrations of therapeutic or prophylactic agents following administration to animals. This invention is also directed to pharmaceutical compositions including and methods using such compounds.

2. State of the Art

Rapid clearance of drugs from the systemic circulation represents a major impediment to effective clinical use of therapeutic and/or prophylactic compounds. Although multiple factors can influence the systemic concentrations of drugs achieved following administration (including drug solubility, dissolution rate, first-pass metabolism, p-glycoprotein and related efflux mechanisms, hepatic/renal elimination, etc), rapid systemic clearance is a particularly significant reason for suboptimal systemic exposure to many compounds. Rapid systemic clearance may require that large doses of drug be administered to achieve a therapeutic or prophylatic effect. Such larger doses of the drug, however, may result in greater variability in drug exposure, more frequent occurrence of side effects, or decrease in patient compliance. Frequent drug administration may also be required to maintain systemic drug levels above a minimum effective concentration. This problem is particularly significant for drugs that must be maintained in a well defined concentration window to provide continuous therapeutic or prophylactic benefit while minimizing adverse effects (including for example, antibacterial agents, antiviral agents, anticancer agents, anticonvulsants, anticoagulants, etc.).

Conventional approaches to extend the systemic exposure of drugs with rapid clearance involve the use of formulation or device approaches that provide a slow or sustained release of drug within the intestinal lumen. These approaches are well known in the art and normally require that the drug be well absorbed from the large intestine, where such formulations are most likely to reside while releasing the drug. Drugs that are amenable to conventional sustained release approaches must be orally absorbed in the intestine and traverse this epithelial barrier by passive diffusion across the apical and basolateral membranes of the intestinal epithelial cells. The physicochemical features of a molecule that favor its passive uptake from the intestinal lumen into the systemic circulation include low molecular weight (e.g.,<500 Da), adequate solubility, and a balance of hydrophobic and hydrophilic character (logP generally 1.5–4.0) (Navia and Chaturvedi, 1996).

Polar or hydrophilic compounds are typically poorly absorbed through an animal's intestine as there is a substantial energetic penalty for passage of such compounds across the lipid bilayers that constitute cellular membranes. Many nutrients that result from the digestion of ingested foodstuffs in animals, such as amino acids, di- and tripeptides, monosaccharides, nucleosides and water-soluable vitamins, are polar compounds whose uptake is essential to the viability of the animal. For these substances there exist specific mechanisms for active transport of the solute molecules across the apical membrane of the intestinal epithelia. This transport is frequently energized by co-transport of ions down a concentration gradient. Solute transporter proteins are generally single sub-unit, multi-transmembrane spanning polypeptides, and upon binding of their substrates are believed to undergo conformational changes which result in movement of the substrate(s) across the membrane.

Over the past 10–15 years, it has been found that a number of orally administered drugs are recognized as substrates by some of these transporter proteins, and that this active transport may largely account for the oral absorption of these molecules (Tsuji and Tamai, 1996). While in most instances the transporter substrate properties of these drugs were unanticipated discoveries made through retrospective analysis, it has been appreciated that, in principle, one might achieve good intestinal permeability for a drug by designing in recognition and uptake by a nutrient transport system. Drugs subject to active absorption in the small intestine are often unable to passively diffuse across epithelial cell membranes and are too large to pass through the tight junctions that exist between the intestinal cells. These drugs include many compounds structurally related to amino acids, dipeptides, sugars, nucleosides, etc. (for example, many cephalosporins, ACE inhibitors, AZT, gabapentin, pregabalin, baclofen, etc.)

Rapid systemic clearance occurs in a portion of these drugs and such clearance requires that they be dosed frequently to maintain a therapeutic or prophylactic concentration in the systemic circulation (Bryans and Wustrow, 1999). Conventional sustained release approaches have not always been successfully applied to these drugs if they are not absorbed from the large intestine. Thus there is a significant need for effective sustained release versions of these drugs, particularly for the pediatric patient population, since drug must be administered during school hours, raising the issues of compliance, liability, and social acceptance.

One attractive pathway that might be exploitable for sustained delivery of drugs with rapid systemic clearance is the entero-hepatic circulation of bile acids (Swaan et al, 1996). Bile acids are hydroxylated steroids that play a key role in digestion and absorption of fat and lipophilic vitamins. After synthesis in the liver, they are secreted into bile and excreted by the gall bladder into the intestinal lumen where they emulsify and help solubilize lipophilic substances. Bile acids are conserved in the body by active uptake from the terminal ileum via the sodium-dependent transporter IBAT (or ASBT) and subsequent hepatic extraction by the transporter NTCP (or LBAT) located in the sinusoidal membrane of hepatocytes. This efficient mechanism to preserve the bile acid pool is termed the enterohepatic circulation (see FIG. 2). In man, the total bile acid pool (3–5 g) recirculates 6–10 times per day giving rise to a daily uptake of approximately 20–30 g of bile acids.

The high transport capacity of the bile acid pathway has been a key reason for interest in this system for drug delivery purposes. Several papers have postulated that chemical conjugates of bile acids with drugs could be used to provide liver site-directed delivery of a drug to bring about high therapeutic concentrations in the diseased liver with minimization of general toxic reactions elsewhere in the body; and gallbladder-site delivery systems of cholecystographic agents and cholesterol gallstone dissolution accelerators" (Ho, 1987). Several groups have explored these concepts in some detail, using the C-24 carboxylic acid, C-3, C-7, and C-12 hydroxyl groups of cholic acid (and other bile acids) as handles for chemically conjugating drugs or drug surrogates. (Kramer et al, 1992; Kim et al, 1993).

The most rigorous drug targeting studies using the bile acid transport pathway to date relate to work with bile acid conjugates of HMG-CoA reductase inhibitors (Kramer et al, 1994b ; Petzinger et al, 1995; Kramer and Wess, 1995; Kramer et al, 1997b). Coupling of the HMG-CoA reductase inhibitor HR 780 via an amide linkage to the C-3 position of cholate, taurocholate and glycocholate afforded substrates for both the ileal and liver bile acid transporter proteins (FIG. 3). Upon oral dosing of rats, the cholate conjugate S 3554 led to specific inhibition of HMG-CoA reductase in the liver, and in contrast to the parent compound HR 780, gave significantly reduced inhibition of the enzyme in extra-hepatic organs. Companion studies that looked at the tissue distribution of radiolabeled drugs two hours after intravenous administration through the mesenteric vein of rats also showed dramatically lower systemic levels for the bile acid conjugate relative to the parent. Because inhibition of HMG-CoA reductase requires the presence of the free carboxylic acid moiety in HR 780 this data was taken to indicate that S 3554 served as a prodrug of HR 780, undergoing hydrolysis (and other uncharacterized metabolism) in the rat liver. Interestingly, uptake of S 3554 by liver did not appear to depend on the liver bile acid transporter NTCP (which prefers taurocholate conjugates), but may instead have involved another multispecific organic anion transport system on the sinusoidal hepatocyte membrane.

In summary, while the concept of harnessing the intestinal bile acid uptake pathway to enhance the absorption of poorly absorbed drugs is well appreciated, the existing art has merely demonstrated that bile acid-drug conjugates may be effectively trafficked to the liver and generally excreted into the bile, either unchanged or as some type of metabolite. The art gives no guidance as to how one prepares a composition that exploits the bile acid transport pathway and simultaneously provides therapeutically meaningful levels of a drug substance outside of the enterohepatic circulation. Furthermore, the art does not describe the potential use of the bile acid transport pathway to achieve a circulating reservoir of conjugated drug that is slowly released into the systemic circulation to provide sustained concentrations.

SUMMARY OF THE INVENTION

This invention is directed to the surprising discovery that the bile acid transport system can be utilized to provide sustained systemic concentrations of drugs administered to an animal. This invention, therefore, permits sustained therapeutic or prophylactic systemic blood concentrations of drugs which heretofore could not be achieved.

Accordingly, in one of its compound aspects, this invention is directed to compounds that provide for sustained therapeutic or prophylactic blood concentrations of a drug or an active metabolite thereof in the systemic circulation of an animal. Such compounds are of formula (I):

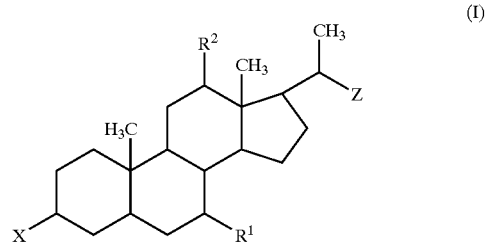

wherein:

$R^1$ and $R^2$ are independently hydrogen or hydroxy;

X is selected from the group consisting of hydroxy and $Q^x$-G- where:

G is —O—, —C(O)O— or —NH—;

$Q^x$ is a group derived from a linear oligopeptide comprising a first moiety D and further comprising from 1 to 3 amino acids, and wherein said group is cleavable from (I) under physiological conditions;

D is a drug containing at least one carboxylic acid group and at least one moiety selected from the group consisting of a primary amino group, a secondary amino group or a hydroxyl group, with the provisos that the drug is not a GABA analog; L-Dopa, an L-aromatic amino acid decarboxylase inhibitor, a catechol O-methyl transferase inhibitor or derivatives thereof; a naturally occurring α-amino acid or an ester or carboxamide of a naturally occurring α-amino acid; a polypeptide derived from a linear oligopeptide containing at least 3 α-amino acids; an oligonucleotide; a cyclophane derivative, a diethylenetriaminopentaacetate derivative, or paramagnetic ion chelates thereof; 5-de-O-methylsporaricin; a bis-(2-chloroethyl)amine containing nitrogen mustard; an HMG-CoA reductase inhibitor; a proline hydroxylase inhibitor; or a steroid containing the carbon substructures of the following formulae:

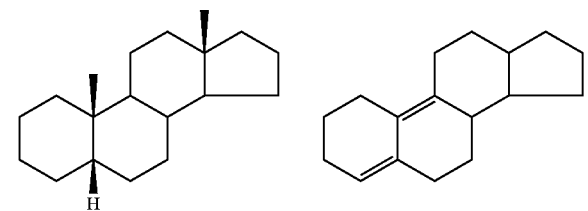

Z is selected from the group consisting of:

(i) a substituted alkyl group containing a moiety which is negatively charged at physiological pH, which moiety is selected from the group consisting of —COOH, —SO$_3$H, —SO$_2$H, —P(O)(OR$^6$)(OH), —OP(O)(OR$^6$)(OH), —OSO$_3$H and the like, and where $R^6$ is selected from the group consisting of alkyl, substituted alkyl, aryl and substituted aryl; and (ii) a group of the formula -M-Q$^{x'}$, wherein M is selected from the group consisting of —CH$_2$OC(O)— and —CH$_2$CH$_2$C(O)—, and wherein Q$^{x'}$ is a group derived from a linear oligopeptide comprising a first moiety D' and further comprising from 1 to 3 amino acids, and wherein said group is cleavable under physiological conditions;

D' is a drug containing at least one carboxylic acid group and at least one moiety selected from the group consisting of a primary amino group, a secondary amino group or a hydroxyl group, with the provisos that the drug is not a GABA analog; L-Dopa, an L-aromatic amino acid decarboxylase inhibitor, a catechol O-methyl transferase inhibitor or derivatives thereof; a naturally occurring α-amino acid or an ester or carboxamide of a naturally occurring α-amino acid; a polypeptide derived from a linear oligopeptide containing at least 3 α-amino acids; an oligonucleotide; a cyclophane derivative, a diethylenetriaminopentaacetate derivative, or paramagnetic ion chelates thereof; 5-de-O-methylsporaricin; a bis-(2-chloroethyl)amine containing nitrogen mustard; an HMG-CoA reductase inhibitor; a proline hydroxylase inhibitor; or a steroid containing the carbon substructures of the following formulae:

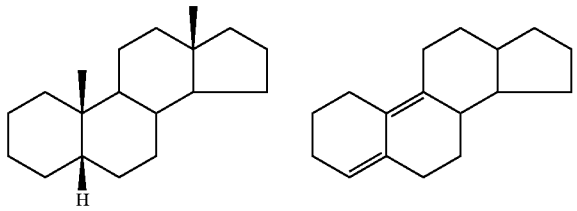

or a pharmaceutically acceptable salt thereof;

provided that when X is hydroxy, then Z is a group of formula -M-Q$^{x'}$.

Preferably, when X is Q$^x$-G-, Q$^x$ is one of the following two structures:

or

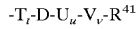

wherein
I is —[NR$^{50}$—(CR$^{51}$R$^{52}$)$_a$—(CR$^{53}$R$^{54}$)$_b$—C(O)]—;
J is —[NR$^{55}$—(CR$^{56}$R$^{57}$)$_c$—(CR$^{58}$R$^{59}$)$_d$—C(O)]—;
K is —[NR$^{60}$—(CR$^{61}$R$^{62}$)$_e$—(CR$^{63}$R$^{64}$)$_f$—C(O)]—;
T is —[C(O)—(CR$^{65}$R$^{66}$)$_g$—(CR$^{67}$R$^{68}$)$_h$—NR$^{69}$]—;
U is —[C(O)—(CR$^{70}$R$^{71}$)$_m$—(CR$^{72}$R$^{73}$)$_n$—NR$^{74}$]—;
V is —[C(O)—(CR$^{75}$R$^{76}$)$_o$—(CR$^{77}$R$^{78}$)$_p$—NR$^{79}$]—;
R$^{40}$ is —OH or —OR$^{17}$;
R$^{41}$ is —H, —C(O)R$^{17}$, or-C(O)OR$^{17}$;
R$^{17}$ is alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

a, b, c, d, e, f, g, h, m, n, o and p are independently 0 or 1, wherein at least one of a and b is 1, at least one of c and d is 1, at least one of e and f is 1, at least one of g and h is 1, at least one of m and n is 1, at least one of o and p is 1;

i, j, k, t, u and v are independently 0 or 1, wherein at least one of i, j and k is 1, and wherein at least one of t, u and v is 1;

R$^{50}$ is hydrogen or R$^{50}$ and R$^{51}$ together with the atoms to which they are attached form a heterocyclyl ring;

R$^{51}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl or R$^{51}$ and R$^{52}$ together with the atoms to which they are attached form a cycloalkyl, substituted cycloalkyl, heterocyclyl or substituted heterocyclyl ring, or R$^{51}$ and R$^{53}$ together with the atoms to which they are attached form a cycloalkyl, substituted cycloalkyl, heterocyclyl or substituted heterocyclyl ring;

R$^{52}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

R$^{53}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or R$^{53}$ and R$^{54}$ together with the atoms to which they are attached form a cycloalkyl, substituted cycloalkyl, heterocyclyl or substituted heterocyclyl ring;

R$^{54}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

R$^{55}$ is hydrogen or R$^{55}$ and R$^{56}$, together with the atoms to which they are attached form a heterocyclyl ring;

R$^{56}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or R$^{56}$ and R$^{57}$ together with the atoms to which they are attached form a cycloalkyl, substituted cycloalkyl, heterocyclyl or substituted heterocyclyl ring, or R$^{56}$ and R$^{58}$ together with the atoms to which they are attached form a cycloalkyl, substituted cycloalkyl, heterocyclyl or substituted heterocyclyl ring;

R$^{57}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

R$^{58}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or R$^{58}$ and R$^{59}$ together with the atoms to which they are attached form a cycloalkyl, substituted cycloalkyl, heterocyclyl or substituted heterocyclyl ring;

R$^{59}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

R$^{60}$ is hydrogen or R$^{60}$ and R$^{61}$, together with the atoms to which they are attached form a heterocyclyl ring;

R$^{61}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or R$^{61}$ and R$^{62}$ together with the atoms to which they are attached form a cycloalkyl, substituted cycloalkyl, heterocyclyl or substituted heterocyclyl ring, or R$^{61}$ and R$^{63}$ together with the atoms to which they are attached form a cycloalkyl, substituted cycloalkyl, heterocyclyl or substituted heterocyclyl ring;

R$^{62}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

R$^{63}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or R$^{63}$ and R$^{64}$ together with the atoms to which they are attached form a cycloalkyl, substituted cycloalkyl, heterocyclyl or substituted heterocyclyl ring;

R$^{64}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

$R^{65}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{65}$ and $R^{66}$ together with the atoms to which they are attached form a cycloalkyl, substituted cycloalkyl, heterocyclyl or substituted heterocyclyl ring, or $R^{65}$ and $R^{67}$ together with the atoms to which they are attached form a cycloalkyl, substituted cycloalkyl, heterocyclyl or substituted heterocyclyl ring;

$R^{66}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

$R^{67}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{67}$ and $R^{68}$ together with the atoms to which they are attached form a cycloalkyl, substituted cycloalkyl, heterocyclyl or substituted heterocyclyl ring;

$R^{68}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

$R^{69}$ is hydrogen or $R^{69}$ and $R^{68}$ together with the atoms to which they are attached form a heterocyclyl ring;

$R^{70}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{70}$ and $R^{71}$ together with the atoms to which they are attached form a cycloalkyl, substituted cycloalkyl, heterocyclyl or substituted heterocyclyl ring, or $R^{70}$ and $R^{72}$ together with the atoms to which they are attached form a cycloalkyl, substituted cycloalkyl, heterocyclyl or substituted heterocyclyl ring;

$R^{71}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

$R^{72}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{72}$ and $R^{73}$ together with the atoms to which they are attached form a cycloalkyl, substituted cycloalkyl, heterocyclyl or substituted heterocyclyl ring;

$R^{73}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

$R^{74}$ is hydrogen or $R^{74}$ and $R^{73}$ together with the atoms to which they are attached form a heterocyclyl ring;

$R^{75}$ is hydrogen, alkyl, substituted alkyl, alkenyl, substituted alkenyl, alknyl, substituted alkynyl, cycloalkyl, substituted cycloalkyl, heterocyclyl, substituted heterocyclyl, aryl, substituted aryl, heteroaryl, substituted heteroaryl or $R^{75}$ and $R^{76}$ together with the atoms to which they are attached form a cycloalkyl, substituted cycloalkyl, heterocyclyl or substituted heterocyclyl ring, or $R^{75}$ and $R^{77}$ together with the atoms to which they are attached form a cycloalkyl, substituted cycloalkyl, heterocyclyl or substituted heterocyclyl ring;

$R^{76}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

$R^{77}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{77}$ and $R^{78}$ together with the atoms to which they are attached form a cycloalkyl, substituted cycloalkyl, heterocyclyl or substituted heterocyclyl ring;

$R^{78}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl; and $R^{79}$ is hydrogen or $R^{79}$ and $R^{78}$ together with the atoms to which they are attached form a heterocyclyl ring;

wherein the bond between $J_J$ or $U_U$ and D and any amino acid to which it is attached is an amide or ester bond, and where the bond between D and $K_k$ or $T_r$ is an amide bond.

Preferably, where Z is a substituted alkyl group of the formula -M-$Q^{x'}$, and wherein $Q^{x'}$ is of the following structure:

wherein

I' is —[$NR^{50'}$—($CR^{51'}R^{52'}$)$_{a'}$—($CR^{53'}R^{54'}$)$_{b'}$—C(O)]—;
J' is —[$NR^{55'}$—($CR^{56'}R^{57'}$)$_{c'}$—($CR^{58'}R^{59'}$)$_{d'}$—C(O)]—;
K' is —[$NR^{60'}$—($CR^{61'}R^{62'}$)$_{e'}$—($CR^{63'}R^{64'}$)$_{f'}$—C(O)]—;
$R^{40'}$ is —OH or —$OR^{17'}$—;
$R^{17'}$ is alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

a', b', c', d', e' and f' are independently 0 or 1, wherein at least one of a' and b' is 1, at least one of c' and d' is 1, at least one of e' and f' is 1;

i', j' and k' are independently 0 or 1, wherein at least one of i', j' and k' is 1;

$R^{50'}$ is hydrogen or $R^{50'}$ and $R^{51'}$ together with the atoms to which they are attached form a heterocyclyl ring;

$R^{51'}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{51'}$ and $R^{52'}$ together with the atoms to which they are attached form a cycloalkyl, substituted cycloalkyl, heterocyclyl or substituted heterocyclyl ring, or $R^{51'}$ and $R^{53'}$ together with the atoms to which they are attached form a cycloalkyl, substituted cycloalkyl, heterocyclyl or substituted heterocyclyl ring;

$R^{52'}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

$R^{53'}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{53'}$ and $R^{54'}$ together with the atoms to which they are attached form a cycloalkyl, substituted cycloalkyl, heterocyclyl or substituted heterocyclyl ring;

$R^{54'}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

$R^{55'}$ is hydrogen or $R^{55'}$ and $R^{56'}$, together with the atoms to which they are attached form a heterocyclyl ring;

$R^{56'}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{56'}$ and $R^{57'}$ together with the atoms to which they are attached form a cycloalkyl, substituted cycloalkyl, heterocyclyl or substituted heterocyclyl ring, or $R^{56'}$ and $R^{58'}$ together with the atoms to which they are attached form a cycloalkyl, substituted cycloalkyl, heterocyclyl or substituted heterocyclyl ring;

$R^{57'}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

$R^{58'}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{58'}$ and $R^{59'}$ together with the atoms to which they are attached form a cycloalkyl, substituted cycloalkyl, heterocyclyl or substituted heterocyclyl ring;

$R^{59'}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

$R^{60'}$ is hydrogen or $R^{60'}$ and $R^{61'}$, together with the atoms to which they are attached form a heterocyclyl ring;

$R^{61'}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{61'}$ and $R^{62'}$ together with the atoms to which they are attached form a cycloalkyl, substituted cycloalkyl, heterocyclyl or substituted heterocyclyl ring, or $R^{61'}$ and $R^{63'}$ together with the atoms to which they are attached form a cycloalkyl, substituted cycloalkyl, heterocyclyl or substituted heterocyclyl ring;

$R^{62'}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

$R^{63'}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{63'}$ and $R^{64'}$ together with the atoms to which they are attached form a cycloalkyl, substituted cycloalkyl, heterocyclyl or substituted heterocyclyl ring;

$R^{64'}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

wherein the bond between $J'_j$ and D' and any amino acid to which it is attached is an amide or ester bond.

Preferably, $R^1$ and $R^2$ of a compound of formula (I) are both α—OH; $R^1$ is β—OH and $R^2$ is hydrogen; $R^1$ is β—OH and $R^2$ is hydrogen; $R^1$ is hydrogen and $R^2$ is α—OH; $R^1$ is β—OH and $R^2$ is α—OH; or $R^1$ and $R^2$ are both hydrogen.

When amino acids I, J, K, T, U and V are included in a compound of formula (I), they are typically derived from naturally occurring α-amino acids.

When amino acids I', J' and K' are included in a compound of formula (I), they are typically derived from naturally occurring α-amino acids.

Preferably, where $Q^x$ of a compound of formula (I) is of the structure -$I_i$-$J_j$-D-$K_k$-$R^{40}$ or -$T_t$-D-$U_u$-$V_v$-$R^{41}$ then b, c, d, e, f, g, h, j, k, m, n, o and p are 0, and a' and i' are 1.

Preferably, where $Q^{x'}$ of a compound of formula (I) is of the structure -$I'_{i'}$-$J'_{j'}$-D'-$K'_{k'}$-$R^{40'}$ then b', c', d', e' and f' are 0, and a' is 1.

Preferably, with respect to substituents included in a compound of formula (I), X is hydroxy and $Q^{x'}$ is -$I'_{i'}$-$J'_{j'}$-D'-$K'_{k'}$-$R^{40'}$.

Preferably in the method, where a compound of formula (I) contains the substituents $R^{50'}$, $R^{51'}$ and $R^{52'}$, the substituents are defined as follows: $R^{50'}$ is hydrogen, $R^{51'}$ is selected from the group consisting of hydrogen, methyl, 2-propyl, 2-butyl, isobutyl, t-butyl, cyclopentyl, cyclohexyl, phenyl, benzyl, 4-hydrocybenzyl, 2-imidazolyl, 2indolyl, —CH$_2$OH, —CH(OH)CH$_3$, —CH$_2$CONH$_2$, —CH$_2$CH$_2$CONH$_2$, —CH$_2$CH$_2$SCH$_3$ or CH$_2$SH, and $R^{52'}$ is hydrogen.

Another aspect of this invention is a compound of formula (II):

(II)

wherein:
$R^1$ and $R^2$ are independently hydrogen or hydroxy;
X is selected from the group consisting of hydroxy and $P^x$-G- where:
G is —O—, —C(O)O— or —NH—;
$P^x$ is a group derived from a linear oligopeptide comprising a first moiety D" and further comprising from 1 to 3 amino acids, and wherein said group is cleavable from (II) under physiological conditions;
D" is a drug containing at least one moiety selected from the group consisting of a primary amino group, a secondary amino group or a hydroxyl group, with the provisos that the drug is not a GABA analog; L-Dopa, an L-aromatic amino acid decarboxylase inhibitor, a catechol O-methyl transferase inhibitor or derivatives thereof; a naturally occurring α-amino acid or an ester or carboxamide of a naturally occurring α-amino acid; a polypeptide derived from a linear oligopeptide containing at least 3 α-amino acids; an oligonucleotide; a cyclophane derivative, a diethylenetriaminopentaacetate derivative, or paramagnetic ion chelates thereof; histamine or tyramine; 5-de-O-methylsporaricin; a bis-(2-chloroethyl)amine containing nitrogen mustard; an HMG-CoA reductase inhibitor; a proline hydroxylase inhibitor; fluvalinate; or a steroid containing the carbon substructures of the following formulae:

Z is selected from the group consisting of:
(i) a substituted alkyl group containing a moiety which is negatively charged at physiological pH, which moiety is selected from the group consisting of —COOH, —SO$_3$H, —SO$_2$H, —P(O)(OR$^6$)(OH), —OP(O)(OR$^6$)(OH), —OSO$_3$H and the like, and where $R^6$ is selected from the group consisting of alkyl, substituted alkyl, aryl and substituted aryl; and (ii) a group of the formula -M-P$^{x'}$, wherein M is selected from the group consisting of —CH$_2$OC(O)— and —CH$_2$CH$_2$C(O)—, and wherein P$^{x'}$ is a group derived from a linear oligopeptide comprising a first moiety D'" and further comprising from 1 to 3 amino acids, and wherein said group is cleavable under physiological conditions;

D'" is a drug containing at least one moiety selected from the group consisting of a primary amino group, a secondary amino group or a hydroxyl group, with the provisos that the drug is not a GABA analog; L-Dopa, an L-aromatic amino acid decarboxylase inhibitor, a catechol O-methyl transferase inhibitor or derivatives thereof; a naturally occurring α-amino acid or an ester or carboxamide of a naturally occurring α-amino acid; a polypeptide derived from a linear oligopeptide containing at least 3 α-amino acids; an oligonucleotide; a cyclophane derivative, a diethylenetriaminopentaacetate derivative, or paramagnetic ion chelates thereof; histamine or tyramine; 5-de-O-methylsporaricin; a bis-(2-chloroethyl)amine containing nitrogen mustard; an HMG-CoA reductase inhibitor; a proline hydroxylase inhibitor; fluvalinate; or a steroid containing the carbon substructures of the following formulae:

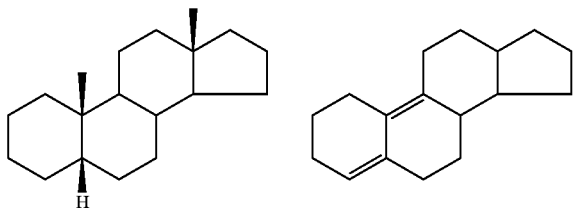

or a pharmaceutically acceptable salt thereof;

provided that when X is hydroxy, then Z is a group of formula -M-P$^{x'}$.

Preferably, X is P$^x$-G-, G is —C(O)O—, and P$^x$ is of the following structure:

wherein

I is —[NR$^{50}$—(CR$^{51}$R$^{52}$)$_a$—(CR$^{53}$R$^{54}$)$_b$—C(O)]—;
J is —[NR$^{55}$—(CR$^{56}$R$^{57}$)$_c$—(CR$^{58}$R$^{59}$)$_d$—C(O)]—;
K is —[NR$^{60}$—(CR$^{61}$R$^{62}$)$_e$—(CR$^{63}$R$^{64}$)$_f$—C(O)]—;

a, b, c, d, e and f are independently 0 or 1, wherein at least one of a and b is 1, at least one of c and d is 1, at least one of e and f is 1;

i, j and k are independently 0 or 1, wherein at least one of i, j and k is 1;

R$^{50}$ is hydrogen or R$^{50}$ and R$^{51}$ together with the atoms to which they are attached form a heterocyclyl ring;

R$^{51}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl or R$^{51}$ and R$^{52}$ together with the atoms to which they are attached form a cycloalkyl, substituted cycloalkyl, heterocyclyl or substituted heterocyclyl ring, or R$^{51}$ and R$^{53}$ together with the atoms to which they are attached form a cycloalkyl, substituted cycloalkyl, heterocyclyl or substituted heterocyclyl ring;

R$^{52}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

R$^{53}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or R$^{53}$ and R$^{54}$ together with the atoms to which they are attached form a cycloalkyl, substituted cycloalkyl, heterocyclyl or substituted heterocyclyl ring;

R$^{54}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

R$^{55}$ is hydrogen or R$^{55}$ and R$^{56}$, together with the atoms to which they are attached form a heterocyclyl ring;

R$^{56}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or R$^{56}$ and R$^{57}$ together with the atoms to which they are attached form a cycloalkyl, substituted cycloalkyl, heterocyclyl or substituted heterocyclyl ring, or R$^{56}$ and R$^{58}$ together with the atoms to which they are attached form a cycloalkyl, substituted cycloalkyl, heterocyclyl or substituted heterocyclyl ring;

R$^{57}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

R$^{58}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or R$^{58}$ and R$^{59}$ together with the atoms to which they are attached form a cycloalkyl, substituted cycloalkyl, heterocyclyl or substituted heterocyclyl ring;

R$^{59}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

R$^{60}$ is hydrogen or R$^{60}$ and R$^{61}$, together with the atoms to which they are attached form a heterocyclyl ring;

R$^{61}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or R$^{61}$ and R$^{62}$ together with the atoms to which they are attached form a cycloalkyl, substituted cycloalkyl, heterocyclyl or substituted heterocyclyl ring, or R$^{61}$ and R$^{63}$ together with the atoms to which they are attached form a cycloalkyl, substituted cycloalkyl, heterocyclyl or substituted heterocyclyl ring;

R$^{62}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

R$^{63}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or R$^{63}$ and R$^{64}$ together with the atoms to which they are attached form a cycloalkyl, substituted cycloalkyl, heterocyclyl or substituted heterocyclyl ring;

R$^{64}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

wherein the bond between K$_k$ and D" and any amino acid to which it is attached is an amide or ester bond.

Preferably, where Z is a substituted alkyl group of the formula -M-P$^{x'}$, P$^{x'}$ is of the following structure:

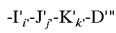

wherein

I' is —[NR$^{50'}$—(CR$^{51'}$R$^{52'}$)$_{a'}$—(CR$^{53'}$R$^{54'}$)$_{b'}$—C(O)]—;
J' is —[NR$^{55'}$—(CR$^{56'}$R$^{57'}$)$_{c'}$—(CR$^{58'}$R$^{59'}$)$_{d'}$—C(O)]—;
K' is —[NR$^{60'}$—(CR$^{61'}$R$^{62'}$)$_{e'}$—(CR$^{63'}$R$^{64'}$)$_{f'}$—C(O)]—;

a', b', c', d', e' and f' are independently 0 or 1, wherein at least one of a' and b' is 1, at least one of c' and d' is 1, at least one of e' and f' is 1;

i', j' and k' are independently 0 or 1, wherein at least one of i', j' and k' is 1;

R$^{50'}$ is hydrogen or R$^{50'}$ and R$^{51'}$ together with the atoms to which they are attached form a heterocyclyl ring;

R$^{51'}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or R$^{51'}$ and R$^{52'}$ together with the atoms to which they are attached form a cycloalkyl, substituted cycloalkyl, heterocyclyl or substituted heterocyclyl ring, or R$^{51'}$ and R$^{53'}$ together with the atoms to which they are attached form a cycloalkyl, substituted cycloalkyl, heterocyclyl or substituted heterocyclyl ring;

R$^{52'}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

R$^{53'}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or R$^{53'}$ and R$^{54'}$ together with the atoms to which they are attached form a cycloalkyl, substituted cycloalkyl, heterocyclyl or substituted heterocyclyl ring;

R$^{54'}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

R$^{55'}$ is hydrogen or R$^{55'}$ and R$^{56'}$, together with the atoms to which they are attached form a heterocyclyl ring;

R$^{56'}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or R$^{56'}$ and R$^{57'}$ together with the atoms to which they are attached form a cycloalkyl, substituted cycloalkyl, heterocyclyl or substituted heterocyclyl ring, or R$^{56'}$ and R$^{58'}$ together with the atoms to which they are attached form a cycloalkyl, substituted cycloalkyl, heterocyclyl or substituted heterocyclyl ring;

R$^{57'}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

R$^{58'}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or R$^{58'}$ and R$^{59'}$ together with the atoms to which they are attached form a cycloalkyl, substituted cycloalkyl, heterocyclyl or substituted heterocyclyl ring;

R$^{59'}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

R$^{60'}$ is hydrogen or R$^{60'}$ and R$^{61'}$, together with the atoms to which they are attached form a heterocyclyl ring;

R$^{61'}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or R$^{61'}$ and R$^{62'}$ together with the atoms to which they are attached form a cycloalkyl, substituted cycloalkyl, heterocyclyl or substituted heterocyclyl ring, or R$^{61'}$ and R$^{63'}$ together with the atoms to which they are attached form a cycloalkyl, substituted cycloalkyl, heterocyclyl or substituted heterocyclyl ring;

R$^{62'}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

R$^{63'}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or R$^{63'}$ and R$^{64'}$ together with the atoms to which they are attached form a cycloalkyl, substituted cycloalkyl, heterocyclyl or substituted heterocyclyl ring;

R$^{64'}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

wherein the bond between K'$_{k'}$ and D''' and any amino acid to which it is attached is an amide or ester bond.

Preferably, R$^1$ and R$^2$ are both α—OH; R$^1$ is β—OH and R$^2$ is hydrogen; R$^1$ is α—OH and R$^2$ is hydrogen; R$^1$ is hydrogen and R$^2$ is α—OH; R$^1$ is β—OH and R$^2$ is α—OH; or R$^1$ and R$^2$ are both hydrogen.

When amino acids I, J and K are included in a compound of Formula II, they are typically derived from naturally occurring α—amino acids.

When amino acids I', J' and K' are included in a compound of Formula II, they are typically derived from naturally occurring α—amino acids.

Preferably, where P$^x$ of a compound of formula II is of the structure -I$_i$-J$_j$-K$_k$D' in Formula II, b, c, d, e, f, j and k are 0, and a and i are 1.

Preferably, where P$^x$ of a compound of formula II is of the structure -I'$_{i'}$-J'$_{j'}$-K'$_{k'}$-D''', b', c', d', e', f', j' and k' are 0, and wherein a' and i' 1.

Yet another aspect of this invention is a compound of formula (III):

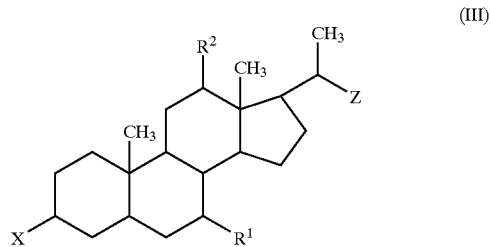

(III)

wherein:

R$^1$ and R$^2$ are independently hydrogen or hydroxy;

X is selected from the group consisting of hydroxy and S$^x$-G- where:

G is —O—, or —NH—;

S$^x$ is a group derived from a linear oligopeptide comprising a first moiety D* and further comprising from 1 to 3 amino acids, and wherein said group is cleavable from (III) under physiological conditions;

D* is a drug containing at least one carboxylic acid group, with the provisos that the drug is not a GABA analog; L-Dopa, an L-aromatic amino acid decarboxylase inhibitor, a catechol O-methyl transferase inhibitor or derivatives thereof; a naturally occurring α-amino acid or an ester or carboxamide of a naturally occurring α-amino acid; a polypeptide derived from a linear oligopeptide containing at least 3 α-amino acids; an oligonucleotide; a cyclophane derivative, a diethylenetriaminopentaacetate derivative, or paramagnetic ion chelates thereof; 5-de-O-methylsporaricin; a bis-(2-chloroethyl)amine containing nitrogen mustard; an HMG-CoA reductase inhibitor; a proline hydroxylase inhibitor; or a steroid containing the carbon substructures of the following formulae:

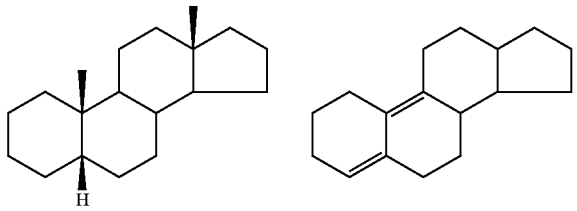

Z is selected from the group consisting of:
a substituted alkyl group containing a moiety which is negatively charged at physiological pH, which moiety is selected from the group consisting of —COOH, —SO$_3$H, —SO$_2$H, —P(O)(OR$^6$)(OH), —OP(O)(OR$^6$)(OH), —OSO$_3$H and the like, and where R$^6$ is selected from the group consisting of alkyl, substituted alkyl, aryl and substituted aryl.

Preferably, X is S$^x$-G-, and S$^x$ is of the following structure:

-T$_t$U$_u$-V$_v$-D* wherein:
T is —[C(O)—(CR$^{65}$R$^{66}$)$_g$—(CR$^{67}$R$^{68}$)$_h$—NR$^{69}$]—;
U is —[C(O)—(CR$^{70}$R$^{71}$)$_m$—(CR$^{72}$R$^{73}$)$_n$—NR$^{74}$]—;
V is —[C(O)—(CR$^{75}$R$^{76}$)$_o$—(CR$^{77}$R$^{78}$)$_p$—NR$^{79}$]—;
g, h, m, n, o and p are independently 0 or 1, wherein at least one of g and h is 1, at least one of m and n is 1, at least one of o and p is 1;
t, u and v are independently 0 or 1, wherein at least one of t, u and v is 1;
R$^{65}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or R$^{65}$ and R$^{66}$ together with the atoms to which they are attached form a cycloalkyl, substituted cycloalkyl, heterocyclyl or substituted heterocyclyl ring, or R$^{65}$ and R$^{67}$ together with the atoms to which they are attached form a cycloalkyl, substituted cycloalkyl, heterocyclyl or substituted heterocyclyl ring;
R$^{66}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;
R$^{67}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or R$^{67}$ and R$^{68}$ together with the atoms to which they are attached form a cycloalkyl, substituted cycloalkyl, heterocyclyl or substituted heterocyclyl ring;
R$^{68}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;
R$^{69}$ is hydrogen or R$^{69}$ and R$^{68}$ together with the atoms to which they are attached form a heterocyclyl ring;

R$^{70}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or R$^{70}$ and R$^{71}$ together with the atoms to which they are attached form a cycloalkyl, substituted cycloalkyl, heterocyclyl or substituted heterocyclyl ring, or R$^{70}$ and R$^{72}$ together with the atoms to which they are attached form a cycloalkyl, substituted cycloalkyl, heterocyclyl or substituted heterocyclyl ring;
R$^{71}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;
R$^{72}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or R$^{72}$ and R$^{73}$ together with the atoms to which they are attached form a cycloalkyl, substituted cycloalkyl, heterocyclyl or substituted heterocyclyl ring;
R$^{73}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;
R$^{74}$ is hydrogen or R$^{74}$ and R$^{73}$ together with the atoms to which they are attached form a heterocyclyl ring;
R$^{75}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or R$^{75}$ and R$^{76}$ together with the atoms to which they are attached form a cycloalkyl, substituted cycloalkyl, heterocyclyl or substituted heterocyclyl ring, or R$^{75}$ and R$^{77}$ together with the atoms to which they are attached form a cycloalkyl, substituted cycloalkyl, heterocyclyl or substituted heterocyclyl ring;
R$^{76}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;
R$^{77}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or R$^{77}$ and R$^{78}$ together with the atoms to which they are attached form a cycloalkyl, substituted cycloalkyl, heterocyclyl or substituted heterocyclyl ring;
R$^{78}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl; and
R$^{79}$ is hydrogen or R$^{79}$ and R$^{78}$ together with the atoms to which they are attached form a heterocyclyl ring;
wherein the bond between V$_v$ and D* and any amino acid to which it is attached is an amide bond.

Preferably, R$^1$ and R$^2$ of Formula III are both α—OH; R$^1$ is β—OH and R$^2$ is hydrogen; R$^1$ is α—OH and R$^2$ is hydrogen; R$^1$ is hydrogen and R$^2$ is α—OH; R$^1$ is β—OH and R$^2$ is α—OH; or R$^1$ and R$^2$ are both hydrogen.

Preferably, when included in a compound of Formula III, amino acids T, U and V are derived from naturally occurring α-amino acids.

Preferably, where S$^x$ of a compound of formula III is of the structure -T$_t$-U$_u$-V$_v$-D*, then h, m, n, o, p, u and v are 0, and g and t are 1.

In a method aspect of this invention, the compounds of this invention are preferably used in a method for achieving sustained therapeutic or prophylactic blood concentrations of a drug, or an active metabolite thereof, in the systemic circulation of an animal. The method involves administering a compound of formula (I), (II), or (III) to an animal.

In a composition aspect of this invention, the compounds of this invention are mixed with a pharmaceutically acceptable carrier to provide a composition. The composition is preferably used in the method of achieving sustained therapeutic or prophylactic blood concentrations of a drug or an active metabolite thereof discussed above.

BRIEF DESCRIPTION OF THE DRAWINGS

FIGS. 4–8 illustrate reaction sequences for preparation of various compounds having a GABA analog substitutent, similar to the compounds of Formula I.

DETAILED DESCRIPTION OF THE INVENTION

Figure 1:
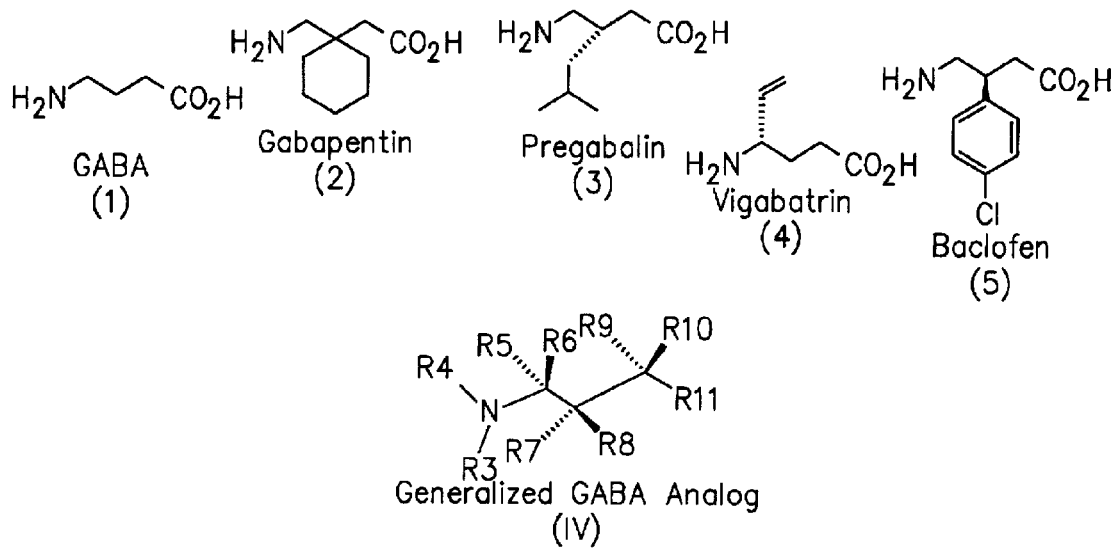
FIG. 1 illustrates structural analogs of γ-aminobutyric acid (GABA).
Figure 2:
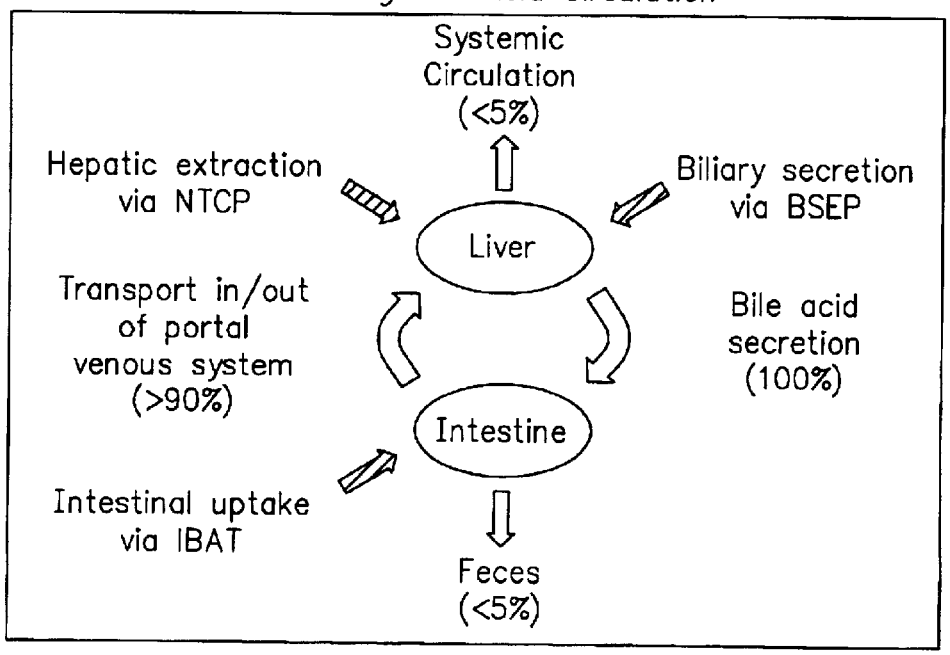
FIG. 2 illustrates the enterohepatic circulation with key transporter proteins identified which mediate bile acid circulation.
Figure 3:
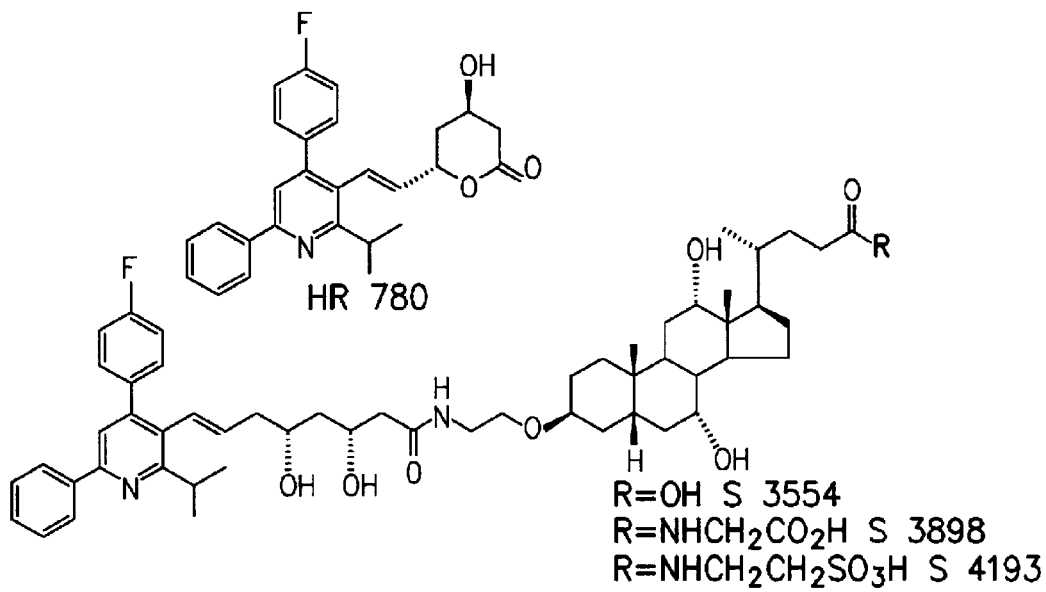
FIG. 3 illustrates HMG-CoA reductase inhibitor HR 780 as well as conjugates employing the lactone-opened ring of HR 780 coupled to a bile acid.

This invention is directed to compounds that provide for sustained systemic concentrations of therapeutic or prophylactic drugs following administration to animals. This invention is also directed to methods using the compounds and pharmaceutical compositions that are used in such methods. However, prior to describing this invention in further detail, the following terms will first be defined:

Definitions

As used herein, the term "animal" refers to various species such as mammalian and avian species including, by way of example, humans, cattle, sheep, horses, dogs, cats, turkeys, chicken, and the like. Preferably, the animal is a mammal and even more preferably is a human.

"Administering to the animal" refers to delivering a compound of formula (I) to an animal through a suitable route. Such routes include, for example, oral, rectal, subcutaneous, intravenous, intramuscular and intranasal. Preferably, the compound is orally administered to the animal.

"Orally delivered drugs" refer to drugs which are administered to an animal in an oral form, preferably, in a pharmaceutically acceptable diluent. Oral delivery includes ingestion of the drug as well as oral gavage of the drug.

"PEPT1 oligopeptide transporter" refers to a type of protein that absorbs peptides in certain tissues, such as the intestine. This transporter is described and characterized in the literature. See Adibi, S. A., *Gastroenterology* 1997, 113, 332–340 and Leibach et al., *Ann. Rev. Nutr.* 1996, 16, 99–119 for a discussion of the transporter.

"PEPT2 oligopeptide transporter" refers to a type of protein that absorbs peptides in certain tissues, such as the kidney. This transporter is described and characterized in the literature. See Dieck, S. T. et al., GLIA 1999, 25, 10–20, Leibach et al., *Ann. Rev. Nutr.* 1996, 16, 99–119; and Wong et al., *Am. J. Physiol.* 1998, 275, C967–C975 for a discussion of the transporter.

"Transported by either a PEPT1 or PEPT2 oligopeptide transporter" refers to the translocation of a molecule across a membrane of a cell expressing the transporter. The translocation occurs through interaction with the transporter and is energized by cotransport of H+ ions across the membrane.

"Amino acid" is intended to denote α-amino acids and β-amino acids only. α-Amino acids are molecules of the formula $HNR^{50}$—$CR^{51}R^{52}$—$C(O)OH$:

wherein:

$R^{50}$ is hydrogen or $R^{50}$ and $R^{51}$ together with the atoms to which they are attached form a heterocyclyl ring;

$R^{51}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{51}$ and $R^{52}$ together with the atoms to which they are attached form a cycloalkyl, substituted cycloalkyl, heterocyclyl or substituted heterocyclyl ring.

β-Amino acids are molecules of formula:

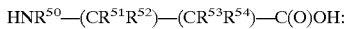

wherein:

$R^{50}$ is hydrogen or $R^{50}$ and $R^{51}$ together with the atoms to which they are attached form a heterocyclyl ring;

$R^{51}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{51}$ and $R^{52}$ together with the atoms to which they are attached form a cycloalkyl, substituted cycloalkyl, heterocyclyl or substituted heterocyclyl ring, or $R^{51}$ and $R^{53}$ together with the atoms to which they are attached form a cycloalkyl, substituted cycloalkyl, heterocyclyl or substituted heterocyclyl ring;

$R^{52}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

$R^{53}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{53}$ and $R^{54}$ together with the atoms to which they are attached form a cycloalkyl, substituted cycloalkyl, heterocyclyl or substituted heterocyclyl ring;

$R^{54}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl.

"Naturally occurring amino acid" refers to any of the alpha-amino acids that are the chief components of proteins. The amino acids are either synthesized by living cells or are obtained as essential components of the diet. Such amino acids include, for example, the following: alanine, arginine, asparagines, aspartic acid, cysteine, glutamine, glutamic acid, glycine, histidine, isoleucine, leucine, lysine, methionine, phenylalanine, proline, serine, threonine, tryptophan, tyrosine and valine.

"Drugs that are either completely or incompletely translocated across the intestinal wall into the systemic blood circulation of an animal" refer to any of the well known orally delivered drugs currently delivered by oral administration as well as drugs which cannot be orally administered because such drugs are insufficiently translocated across the intestinal wall of an animal to provide therapeutic or prophylactic blood concentrations in said animal.

Preferably, drugs that fall into the following categories:

(i) drugs which are insufficiently translocated across the intestinal wall to provide therapeutic or prophylactic blood concentrations;

(ii) incompletely translocated drugs; or (iii) drugs that are either completely or incompletely translocated across the intestinal wall into the systemic blood circulation of an animal, contain suitable functionality to provide points of linkage in forming compounds of formula (I), (II) and (III) above. Such functionality includes, by way of example, carboxyl groups, amine groups and hydroxyl groups.

Examples of drugs containing carboxyl groups include, for instance, angiotensin-converting enzyme inhibitors such as alecapril, 1-[4-carboxy-2-methyl-2R,4R-pentanoyl]-2,3-dihydro-2S-indole-2-carboxylic acid, enalaprilic acid, lisinopril, N-cyclopentyl-N-[3-[(2,2-dimethyl-1-oxopropyl)thio]-2-methyl-1-oxoproplyl]glycine, pivopril, quinaprilat, (2R, 4R)-2-hydroxyphenyl)-3-(3-mercaptopropionyl)-4-thiazolidinecarboxylic acid, (S) benzamido-4-oxo-6-phenylhexenoyl-2-carboxypyrrolidine, [2S-1[R*(R*))]] 2α, 3αβ, 7αβ]-1 [2-[[1-carboxy-3phenylpropyl]-amino]-1-oxopropyl]octahydro-1H-indole-2-carboxylic acid, [3S-1[R*]-2-[2[[1-carboxy-3-phenylpropyl]-amino]-1-oxypropyl]-1,2,3,4-tetrahydro-3-isoquinolone carboxylic acid and tiopronin; cephalosporin antibiotics such as cefaclor, cefadroxil, cefamandole, cefatrizine, cefazedone, cefazuflur, cefazolin, cefbuperazone, cefixime, cefmenoxime, cefmetazole, cefodizime, cefonicid, cefoperazone, ceforanide, cefotaxime, cefotefan, cefotiam, cefoxitin, cefpimizole, cefpirome, cefpodoxime, cefroxadine, cefsulodin, cefpiramide, ceftazidime, ceftezole, ceftizoxime, ceftriaxone, cefuroxime, cephacetrile, cephalexin, cephaloglycin, cephaloridine, cephalosporin, cephanone, cephradine and latamoxef; penicillins such as amoxycillin, ampicillin, apalcillin, azidocillin, azlocillin, benzylpencillin, carbenicillin, carfecillin, carindacillin, cloxacillin, cyclacillin, dicloxacillin, epicillin, flucloxacillin, hetacillin, methicillin, mezlocillin, nafcillin, oxacillin, phenethicillin, piperazillin, sulbenicillin, temocillin and ticarcillin; thrombin inhibitors such as argatroban, melagatran and napsagatran; influenza neuraminidase inhibitors such as zanamivir and BCX-1812; non-steroidal antiinflammatory agents such as acametacin, alclofenac, alminoprofen, aspirin (acetylsalicylic acid), 4-biphenylacetic acid, bucloxic acid, carprofen, cinchofen, cinmetacin, clometacin, clonixin, diclenofac, diflunisal, etodolac, fenbufen, fenclofenac, fenclosic acid, fenoprofen, ferobufen, flufenamic acid, flufenisal, flurbiprofm, fluprofen, flutiazin, ibufenac, ibuprofen, indomethacin, indoprofen, ketoprofen, ketorolac, lonazolac, loxoprofen, meclofenamic acid, mefenamic acid, 2-(8-methyl-10,11-dihydro-11-oxodibenz[b,f]oxepin-2-yl)propionic acid, naproxen, nifluminic acid, O-(carbamoylphenoxy)acetic acid, oxoprozin, pirprofen, prodolic acid, salicylic acid, salicylsalicylic acid, sulindac, suprofen, tiaprofenic acid, tolfenamic acid, tolmetin and zopemirac; prostaglandins such as ciprostene, 16-deoxy-16-hydroxy-16-vinyl prostaglandin $E_2$, 6,16-dimethylprostaglandin $E_2$, epoprostostenol, meteneprost, nileprost, prostacyclin, prostaglandins $E_1$, $E_2$, or $F_{2\alpha}$ and thromboxane $A_2$; quinolone antibiotics such as acrosoxacin, cinoxacin, ciprofloxacin, enoxacin, flumequine, naladixic acid, norfloxacin, ofloxacin, oxolinic acid, pefloxacin, pipemidic acid and piromidic acid; other antibiotics such as aztreonam, imipenem, meropenem and related carbopenem antibiotics.

Representative drugs containing amine groups include: acebutalol, albuterol, alprenolol, atenolol, bunolol, bupropion, butopamine, butoxamine, carbuterol, cartelolol, colterol, deterenol, dexpropanolol, diacetolol, dobutamine, exaprolol, exprenolol, fenoterol, fenyripol, labotolol, levobunolol, metolol, metaproterenol, metoprolol, nadolol, pamatolol, penbutalol, pindolol, pirbuterol, practolol, prenalterol, primidolol, prizidilol, procaterol, propanolol, quinterenol, rimiterol, ritodrine, solotol, soterenol, sulfiniolol, sulfinterol, sulictidil, tazaolol, terbutaline, timolol, tiprenolol, tipridil, tolamolol, thiabendazole, albendazole, albutoin, alendronate, alinidine, alizapride, amiloride, aminorex, aprinocid, cambendazole, cimetidine, cisapride, clonidine, cyclobenzadole, delavirdine, efegatrin, etintidine, fenbendazole, fenmetazole, flubendazole, fludorex, icadronate, lobendazole, mebendazole, metazoline, metoclopramide, methylphenidate, mexiletine, neridronate, nocodazole, oxfendazole, oxibendazole, oxmetidine, pamidronate, parbendazole, pramipexole, prazosin, procainamide, ranitidine, tetrahydrazoline, tiamenidine, tinazoline, tiotidine, tocainide, tolazoline, tramazoline, xylometazoline, dimethoxyphenethylamine, N-[3(R)-[2-piperidin-4-yl)ethyl]-2-piperidone-1-yl]acetyl-3(R)-methyl-β-alanine, adrenolone, aletamine, amidephrine, amphetamine, aspartame, bamethan, betahistine, clorprenaline, chlortermine, ephrinephrine etryptamine, fenfluramine, methyldopamine, norepinephrine, tocainide, enviroxime, nifedipine, nimodipine, triamterene, norfloxacin and similar compounds such as pipedemic acid, 1 -ethyl-6-fluoro-1,4dihydro-4-oxo-7-(1-piperazinyl)-1,8-napthyridine-3-carboxylic acid, 1-cyclopropyl-6-fluoro-1,4-dihydro-4-oxo-7-(piperazinyl)-3-quinolinecarboxylic acid.

Representative drugs containing hydroxy groups include: steroidal hormones such as allylestrenol, cingestol, dehydroepiandrosteron, dienostrol, diethylstilbestrol, dimethisteron, ethyneron, ethynodiol, estradiol, estron, ethinyl estradiol, ethisteron, lynestrenol, mestranol, methyl testosterone, norethindron, norgestrel, norvinsteron, oxogeston, quinestrol, testosteron and tigestol; tranquilizers such as dofexazepam, hydroxyzin, lorazepam and oxazepam; neuroleptics such as acetophenazine, carphenazine, fluphenazine, perphenyzine and piperaetazine; cytostatics such as aclarubicin, cytarabine, decitabine, daunorubicin, dihydro-5-azacytidine, doxorubicin, epirubicin, estramustin, etoposide, fludarabine, gemcitabine, 7-hydroxychlorpromazin, nelarabine, neplanocin A, pentostatin, podophyllotoxin, tezacitabine, troxacitabine, vinblastin, vincristin, vindesin; hormones and hormone antagonists such as buserilin, gonadoliberin, icatibrant and leuprorelin acetate; antihistamines such as terphenadine; analgesics such as diflunisal, naproxol, paracetamol, salicylamide and salicyclic acid; antibiotics such as azidamphenicol, azithromycin, camptothecin, cefamandol, chloramphenicol, clarithromycin, clavulanic acid, clindamycin, demeclocyclin, doxycyclin, erythromycin, gentamycin, imipenem, latamoxef, metronidazole, neomycin, novobiocin, oleandomycin, oxytetracyclin, tetracycline, thiamenicol and tobramycin; antivirals such as acyclovir, d4C, ddC, DMDC, Fd4C, FddC, FMAU, FTC, 2'-fluoro-ara-dideoxyinosine, ganciclovir, lamivudine, penciclovir, SddC, stavudine, 5-trifluoromethyl-2'-deoxyuridine, zalcitabine and zidovudine; bisphosphonates such as EB-1053, etidronate, ibandronate, olpadronate, residronate, YH-529 and zolendronate; protease inhibitors such as ciprokiren, enalkiren, ritonavir, saquinavir and terlakiren; prostaglandins such as arbaprostil, carboprost, misoprostil and prostacydin; antidepressives such as 8-hydroxychlorimipramine and 2-hydroxyimipramine; antihypertonics such as sotarol and fenoldopam; anticholinerogenics such as biperidine, procyclidin and trihexyphenidal; antiallergenics such as cromolyn; glucocorticoids such as betamethasone, budenosid, chlorprednison, clobetasol, clobetasone, corticosteron, cortisone, cortodexon, dexamethason, flucortolon, fludrocortisone, flumethasone, flunisolid, fluprednisolon, flurandrenolide, flurandrenolon acetonide, hydrocortisone, meprednisone, methylpresnisolon, paramethasone, prednisolon, prednisol, triamcinolon and triamcinolon acetonide; narcotic agonists and antagonists such as apomorphine, buprenorphine, butorphanol, codein, cyclazocin, hydromorphon, ketobemidon, levallorphan, levorphanol, metazocin, morphine, nalbuphin, nalmefen, naloxon, nalorphine, naltrexon, oxycodon, oxymorphon and pentazocin; stimulants such asmazindol and pseudoephidrine; anaesthetics such as hydroxydion and propofol; β-receptor blockers such as acebutolol, albuterol, alprenolol, atenolol, betazolol, bucindolol, cartelolol, celiprolol, cetamolol, labetalol, levobunelol, metoprolol, metipranolol, nadolol, oxyprenolol, pindolol, propanolol and timolol; α-sympathomimetics such as adrenalin, metaraminol, midodrin, norfenefrin, octapamine, oxedrin, oxilofrin, oximnetazolin and phenylefrin; β-sympathomimetics such as bamethan, clenbuterol, fenoterol, hexoprenalin, isoprenalin, isoxsuprin, orciprenalin, reproterol, salbutamol and terbutalin; bronchodilators such as carbuterol, dyphillin, etophyllin, fenoterol, pirbuterol, rimiterol and terbutalin; cardiotonics such as digitoxin, dobutamin, etilefrin and prenalterol; antimycotics such as amphotericin B, chlorphenesin, nystatin and perimycin; anticoagulants such as acenocoumarol, dicoumarol, phenprocoumon and warfarin; vasodilators such as bamethan, dipyrimadol, diprophyllin, isoxsuprin, vincamin and xantinol nicotinate; antihypocholesteremics such as compactin, eptastatin, mevinolin and simvastatin; miscellaneous drugs such as bromperidol (antipsychotic), dithranol (psoriasis) ergotamine (migraine) ivermectin (antihelminthic), metronidazole and secnizadole (antiprotozoals), nandrolon (anabolic), propafenon and quinadine (antiarythmics), quetiapine (CNS), serotonin (neurotransmitter) and silybin (hepatic disturbance).

It is understood that the drug is not a GABA analog; L-Dopa, an L-aromatic amino acid decarboxylase inhibitor, a catechol O-methyl transferase inhibitor or derivatives thereof; a naturally occurring α-amino acid or an ester or carboxamide of a naturally occurring α-amino acid; a polypeptide derived from a linear oligopeptide containing at least 3 α-amino acids; an oligonucleotide; a cyclophane derivative, a diethylenetriaminopentaacetate derivative, or paramagnetic ion chelates thereof; histamine or tyramine; 5-de-O-methylsporaricin; a bis-(2-chloroethyl)amine containing nitrogen mustard; an HMG-CoA reductase inhibitor; a proline hydroxylase inhibitor; fluvalinate; or a steroid containing the carbon substructures of the following formulae:

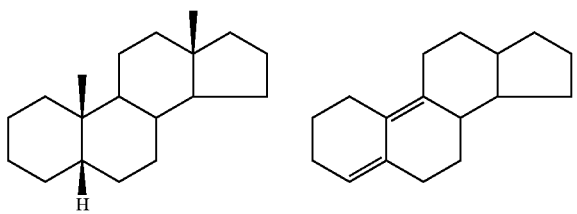

"GABA analog" refers to a compound of one of the following formulae:

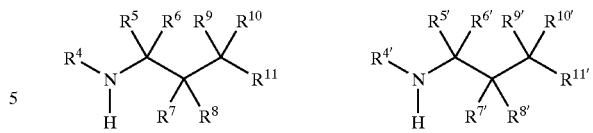

wherein:
$R^4$ is hydrogen, or $R^4$ and $R^9$ together with the atoms to which they are attached form a heterocyclic ring;
$R^5$ and $R^6$ are independently selected from the group consisting of hydrogen, alkyl, substituted alkyl, alkenyl, substituted alkenyl, alkynyl, aryl, substituted aryl, heteroaryl and substituted heteroaryl;
$R^7$ and $R^8$ are independently selected from the group consisting of hydrogen, alkyl, substituted alkyl, alkenyl, alkynyl, aryl, substituted aryl, heteroaryl and substituted heteroaryl, or $R^7$ and $R^8$ together with the atoms to which they are attached form a cycloalkyl, substituted cycloalkyl, heterocyclic or substituted heterocyclic ring;
$R^9$ is selected from the group consisting of hydrogen, alkyl, substituted alkyl, alkenyl, alkynyl, aryl, substituted aryl, heteroaryl and substituted heteroaryl;
$R^{10}$ is selected from the group consisting of hydrogen, alkyl, substituted alkyl, alkenyl, alkynyl, aryl, substituted aryl, heteroaryl and substituted heteroaryl;
$R^{11}$ is selected from the group consisting of carboxylic acid, carboxylic amide, carboxylic ester, sulfonamide, phosphonic acid, acidic heterocycle, sulfonic acid and hydroxamic acid;
$R^{4'}$ is hydrogen, or $R^{4'}$ and $R^{9'}$ together with the atoms to which they are attached form a heterocyclic ring;
$R^{5'}$ and $R^{6'}$ are independently selected from the group consisting of hydrogen, alkyl, substituted alkyl, alkenyl, substituted alkenyl, alkynyl, aryl, substituted aryl, heteroaryl and substituted heteroaryl;
$R^{7'}$ and $R^{8'}$ are independently selected from the group consisting of hydrogen, alkyl, substituted alkyl, alkenyl, alkynyl, aryl, substituted aryl, heteroaryl and substituted heteroaryl, or $R^{7'}$ and $R^{8'}$ together with the atoms to which they are attached form a cycloalkyl, substituted cycloalkyl, heterocyclic or substituted heterocyclic ring;
$R^{9'}$ is selected from the group consisting of hydrogen, alkyl, substituted alkyl, alkenyl, alkynyl, aryl, substituted aryl, heteroaryl and substituted heteroaryl;
$R^{10'}$ is selected from the group consisting of hydrogen, alkyl, substituted alkyl, alkenyl, alkynyl, aryl, substituted aryl, heteroaryl and substituted heteroaryl;
$R^{11'}$ is selected from the group consisting of carboxylic acid, carboxylic amide, carboxylic ester, sulfonamide, phosphonic acid, acidic heterocycle, sulfonic acid and hydroxamic acid.

"Catechol O-methyl transferase inhibitor" preferably refers to catechol O-methyl transferase inhibitors such as entacapone, nitecapone and tolcapone optionally with one or two hydrogen atoms of two hydroxyl groups of the catechol group replaced with $-C(O)R^{44}$, $-C(O)OR^{45}$ and/or $-OCR^{43}R^{44}OC(O)R^{45}$, wherein $R^{43}$ and $R^{44}$ independently are members selected from the group consisting of hydrogen, alkyl, substituted alkyl, cycloalkyl, substituted cycloalkyl, aryl, substituted aryl, aralkyl, substituted aralkyl, heteroaryl and substituted heteroaryl, or $R^{43}$ and $R^{44}$ together with the carbon atom to which they are attached form a cycloalkyl, substituted cycloalkyl, heterocycle or substituted heterocyclic ring, $R^{45}$ is selected from the group consisting of alkyl, substituted alkyl, cycloalkyl, substituted cycloalkyl, aryl, substituted aryl, aralkyl, substituted aralkyl, heteroaryl and substituted heteroaryl, or the OH group of the carboxyl moiety is replaced by —OR$^{44}$.

"An inhibitor of L-aromatic amino acid decarboxylase" preferably refers to L-aromatic amino acid decarboxylase inhibitors such as carbidopa and benzserazide optionally with a hydrogen atom of the amino or the hydrazido group of the L-aromatic amino acid decarboxylase inhibitor replaced with —C(O)R$^{104}$, —C(O)OR$^{105}$ or an amino acid group, wherein R$^{104}$ is selected from the group consisting of hydrogen, alkyl, substituted alkyl, cycloalkyl, substituted cycloalkyl, aryl, substituted aryl, aralkyl, substituted aralkyl, heteroaryl and substituted heteroaryl, and R$^{105}$ is selected from the group consisting of alkyl, substituted alkyl, cycloalkyl, substituted cycloalkyl, aryl, substituted aryl, aralkyl, substituted aralkyl, heteroaryl and substituted heteroaryl; and/or optionally with one or two hydrogen atoms of the two —OH groups of the catechol or the three —OH groups of the pyrogallol group of the L-aromatic amino acid decarboxylase inhibitor are replaced with —C(O)R$^{104}$, —C(O)OR$^{105}$ and/or —OCR$^{103}$R$^{104}$OC(O)R$^{105}$ wherein R$^{105}$ is defined as above, R$^{103}$ and R$^{104}$ independently are members selected from the group consisting of hydrogen, alkyl, substituted alkyl, cycloalkyl, substituted cycloalkyl, aryl, substituted aryl, aralkyl, substituted aralkyl, heteroaryl and substituted heteroaryl, or R$^{103}$ and R$^{104}$ together with the carbon atom to which they are attached form a cycloalkyl, substituted cycloalkyl, heterocycle or substituted heterocyclic ring; or optionally with two adjacent —OH groups of the catechol or pyrogallol group protected with a 5-membered cyclic carbonate or 2,3-dioxo-1,4-dioxane ortho fused with a benzene ring of the catechol or pyrogallol group; and/or the OH group of the carboxyl moiety is replaced by —OR$^{104}$.

"Derivatives of L-DOPA" preferably refers to L-DOPA molecules wherein:

a) a hydrogen atom of the amino group of the L-DOPA molecule is replaced with —C(O)R$^{114}$, —C(O)OR$^{115}$ or an amino acid group, wherein R$^{114}$ is selected from the group consisting of hydrogen, alkyl, substituted alkyl, cycloalkyl, substituted cycloalkyl, aryl, substituted aryl, aralkyl, substituted aralkyl, heteroaryl and substituted heteroaryl, and R$^{115}$ is selected from the group consisting of alkyl, substituted alkyl, cycloalkyl, substituted cycloalkyl, aryl, substituted aryl, aralkyl, substituted aralkyl, heteroaryl and substituted heteroaryl; and/or b) one or two hydrogen atoms of the two —OH groups of the catechol group of the L-DOPA molecule are replaced with —C(O)R$^{114}$, —C(O)OR$^{115}$ and/or —OCR$^{113}$R$^{114}$OC(O)R$^{115}$ wherein R$^{115}$ is defined as above, R$^{113}$ and R$^{114}$ independently are members selected from the group consisting of hydrogen, alkyl, substituted alkyl, cycloalkyl, substituted cycloalkyl, aryl, substituted aryl, aralkyl, substituted aralkyl, heteroaryl and substituted heteroaryl, or R$^{113}$ and R$^{114}$ together with the carbon atom to which they are attached form a cycloalkyl, substituted cycloalkyl, heterocycle or substituted heterocyclic ring, or the two —OH groups of the catechol group of the L-DOPA molecule are protected with a 5-membered cyclic carbonate or 2,3-dioxo-1,4-dioxane ortho fused with a benzene ring of the catechol group of the L-DOPA molecule; and/or c) the OH group of the carboxyl moiety is replaced by —OR$^{114}$.

"Acidic heterocycle" refers to a reprotonatable heterocycle having a pKa less than 7.0. Examples of such heterocycles include the following:

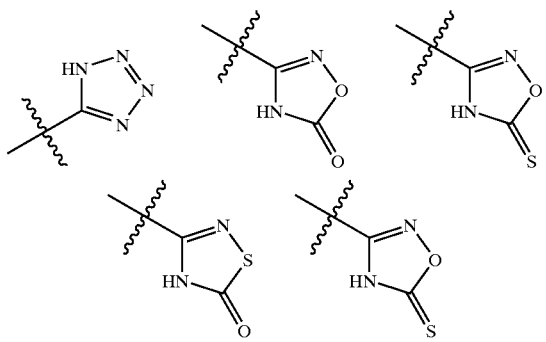

"Linear oligopeptide" refers to an amide oligomer comprising either a terminal amino group or a terminal carboxylic acid group or (preferably) both a terminal amino group and a terminal carboxylic acid group, which oligomer is formed by condensation of the terminal amino residue of at least one amino acid with the terminal carboxylic acid residue of at least a second amino acid. The amino acids comprising the oligopeptide are either α-amino acids, β-amino acids, or a mixture of α-amino acids and β-amino acids. Note that when an α-amino acid additionally contains either a β-amino group or a β-carboxylic acid group (e.g. as in aspartic acid) a linear oligopeptide formed from such an amino acid is intended to imply that it is the α-amine or α-carboxylic acid moiety (or both) of such residue that is involved in amide formation.

"Derived from a compound" or "derivative" refers to a moiety that is structurally related to such a compound. The structure of the moiety is identical to the compound except at 1 or 2 positions. At these positions either a hydrogen atom attached to a heteroatom, or a hydroxyl moiety of a carboxylic, phosphonic, phosphoric or sulfonic acid group has been replaced with a covalent bond that serves as a point of attachment to another moiety. For example, the moiety:

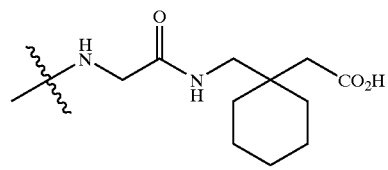

is derived from a linear oligopeptide comprising glycine and the drug gabapentin. In this moiety, a hydrogen atom has been replaced with a covalent bond. "Derived from a linear oligopeptide" is meant to specifically denote that the point of attachment is either the terminal amino group or the terminal acid group of the oligopeptide.

The term "systemic bioavailability" refers to the rate and extent of systemic exposure to a drug or a metabolite thereof as reflected by the area under the systemic blood concentration versus time curve.

"Translocation across the intestinal wall" refers to movement of a drug or drug conjugate by a passive or active mechanism, or both, across an epithelial cell membrane of any region of the gastrointestinal tract.

"Active metabolite of a drug" refers to products of in vivo modification of the drug which have therapeutic or prophylactic effect.

"Therapeutic or prophylactic blood concentrations" refers to systemic exposure to a sufficient concentration of a drug or an active metabolite thereof over a sufficient period of time to effect disease therapy or to prevent the onset or reduce the severity of a disease in the treated animal.

"Sustained release" refers to release of a drug or an active metabolite thereof into the systemic circulation over a prolonged period of time relative to that achieved by oral administration of a conventional formulation of the drug.

"Tissue of the enterohepatic circulation" refers to the blood, plasma, intestinal contents, intestinal cells, liver cells, biliary tract or any fraction, suspension, homogenate, extract or preparation thereof.

"Conjugating" refers to the formation of a covalent bond.

"Bile acid transport system" refers to any membrane transporter protein capable of causing a bile acid or a derivative thereof to be translocated across a membrane of a cell of the gastrointestinal tract or liver.

"Active transport or active transport mechanism" refers to the movement of molecules across cellular membranes that: a) is directly or indirectly dependent on an energy mediated process (i.e. driven by ATP hydrolysis, ion gradient, etc); or b) occurs by facilitated diffusion mediated by interaction with specific transporter proteins; or c) occurs through a modulated solute channel.

"A moiety selected to permit a compound of formula (I) to be translocated across the intestinal wall of an animal via the bile acid transport system" refers to compounds which, when conjugated to the drug (directly or via a linker moiety), are translocated across the intestinal wall via the bile acid transport system. Evaluation of which candidate compounds can be so translocated across the intestinal wall can be conducted by the in vitro assay set forth in Example 3 below.

"Practical dosage regimen" refers to a schedule of drug administration that is practical for a patient to comply with. For human patients, a practical dosage regimen for an orally administered drug is likely to be an aggregate dose of less than 10 g/day.

"Amino-protecting group" or "amino-blocking group" refers to any group which when bound to one or more amino groups prevents reactions from occurring at these amino groups and which protecting groups can be removed by conventional chemical steps to reestablish the amino group. The particular removable blocking group is not critical and preferred amino blocking groups include, by way of example only, t-butyoxycarbonyl (t-BOC), benzyloxycarbonyl (CBZ), and the like.

"Carboxyl-protecting group" or "carboxyl-blocking group" refers to any group which when bound to one or more carboxyl groups prevents reactions from occurring at these groups and which protecting groups can be removed by conventional chemical steps to reestablish the carboxyl group. The particular removable blocking group is not critical and preferred carboxyl blocking groups include, by way of example only, esters of the formula —COOR" where R" is selected from the group consisting of alkyl, substituted alkyl, alkenyl, substituted alkenyl, aryl, substituted aryl, alkaryl, substituted alkaryl, cycloalkyl, substituted cycloalkyl, heteroaryl, substituted heteroaryl, heterocyclic, and substituted heterocyclic.

"Alkyl" refers to alkyl groups preferably having from 1 to 20 carbon atoms and more preferably 1 to 6 carbon atoms. This term is exemplified by groups such as methyl, t-butyl, n-heptyl, octyl, dodecyl and the like.

"Substituted alkyl" refers to an alkyl group, preferably of from 1 to 20 carbon atoms, having from 1 to 5 substituents selected from the group consisting of alkoxy, substituted alkoxy, acyl, acylamino, thiocarbonylamino, acyloxy, amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxylaryl, substituted aryloxyaryl, cyano, halogen, hydroxyl, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted aryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, OS(O)$_2$-heterocyclic, —OS(O)$_2$-substituted heterocyclic, —OSO2-NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$-NR-substituted alkyl, —NRS(O)$_2$—NR-aryl, —NRS(O)$_2$—NR-substituted aryl, —NRS(O)$_2$-NR-heteroaryl, —NRS(O)$_2$—NR-substituted heteroaryl, —NRS(O)$_2$-NR-heterocyclic, —NRS(O)$_2$-NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and substituted alkyl groups having amino groups blocked by conventional blocking groups such as Boc, Cbz, formyl, and the like or alkyl/substituted alkyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Alkoxy" refers to the group "alkyl-O—" which includes, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Substituted alkoxy" refers to the group "substituted alkyl-O—". "Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)—wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acylamino" refers to the group —C(O)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thiocarbonylamino" refers to the group —C(S)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form, together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O—wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to alkenyl group preferably having from 2 to 20 carbon atoms and more preferably 2 to 6 carbon atoms and having at least 1 and preferably from 1–2 sites of alkenyl unsaturation.

"Substituted alkenyl" refers to alkenyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxylcycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic, substituted heterocyclic and substituted alkenyl groups having amino groups blocked by conventional blocking groups such as Boc, Cbz, formyl, and the like or alkenyl/substituted alkenyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Alkenyloxy" refers to the group —O-alkenyl.

"Substituted alkenyloxy" refers to the group —O-substituted alkenyloxy.

"Alkynyl" refers to alkynyl group preferably having from 2 to 20 carbon atoms and more preferably 3 to 6 carbon atoms and having at least 1 and preferably from 1–2 sites of alkynyl unsaturation.

"Substituted alkynyl" refers to alkynyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxylcycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic, substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Alkylene" refers to a divalent alkylene group preferably having from 1 to 20 carbon atoms and more preferably 1 to 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" refers to alkylene groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxylcycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic, substituted heterocyclic and substituted alkenyl groups having amino groups blocked by conventional blocking groups such as Boc, Cbz, formyl, and the like or alkenyl/substituted alkenyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Alkenylene" refers to a divalent alkenylene group preferably having from 2 to 20 carbon atoms and more preferably 1 to 6 carbon atoms and having from 1 to 2 sites of alkenyl unsaturation. This term is exemplified by groups such as ethenylene (—CH=CH—), propenylene (—CH$_2$CH=CH—), and the like.

"Substituted alkenylene" refers to alkenylene groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxylcycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic, substituted heterocyclic and substituted alkenyl groups having amino groups blocked by conventional blocking groups such as Boc, Cbz, formyl, and the like or alkenyl/substituted alkenyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$- heteroaryl, —SO₂-substituted heteroaryl, —SO₂-heterocyclic, —SO₂-substituted heterocyclic and —SO₂NRR where R is hydrogen or alkyl.

"Alkynylene" refers to a divalent alkynylene group preferably having from 2 to 20 carbon atoms and more preferably 1 to 6 carbon atoms and having from 1 to 2 sites of alkynyl unsaturation. This term is exemplified by groups such as ethynylene, propynylene and the like.

"Substituted alkynylene" refers to alkynylene groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)₂-alkyl, —OS(O)₂-substituted alkyl, —OS(O)₂-aryl, —OS(O)₂-substituted aryl, —OS(O)₂-heteroaryl, —OS(O)₂-substituted heteroaryl, —OS(O)₂-heterocyclic, —OS(O)₂-substituted heterocyclic, —OSO₂—NRR where R is hydrogen or alkyl, —NRS(O)₂-alkyl, —NRS(O)₂-substituted alkyl, —NRS(O)₂-aryl, —NRS(O)₂-substituted aryl, —NRS(O)₂-heteroaryl, —NRS(O)₂-substituted heteroaryl, —NRS(O)₂-heterocyclic, —NRS(O)₂-substituted heterocyclic, —NRS(O)₂—NR-alkyl, —NRS(O)₂—NR-substituted alkyl, —NRS(O)₂—NR-aryl, —NRS(O)₂—NR-substituted aryl, —NRS(O)₂—NR-heteroaryl, —NRS(O)₂—NR-substituted heteroaryl, —NRS(O)₂—NR-heterocyclic, —NRS(O)₂—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic, substituted heterocyclic and substituted alkenyl groups having amino groups blocked by conventional blocking groups such as Boc, Cbz, formyl, and the like or alkenyl/substituted alkenyl groups substituted with —SO₂-alkyl, —SO₂-substituted alkyl, —SO₂-alkenyl, —SO₂-substituted alkenyl, —SO₂-cycloalkyl, —SO₂-substituted cycloalkyl, —SO₂-aryl, —SO₂-substituted aryl, —SO₂-heteroaryl, —SO₂-substituted heteroaryl, —SO₂-heterocyclic, —SO₂-substituted heterocyclic and —SO₂NRR where R is hydrogen or alkyl.

"Amidino" refers to the group H₂NC(=NH)— and the term "alkylamidino" refers to compounds having 1 to 3 alkyl groups (e.g., alkylHNC(=NH)—).

"Thioamidino" refers to the group RSC(=NH)— where R is hydrogen or alkyl.

"Aminoacyl" refers to the groups —NRC(O)alkyl, —NRC(O)substituted alkyl, —NRC(O)cycloalkyl, —NRC(O)substituted cycloalkyl, —NRC(O)alkenyl, —NRC(O)substituted alkenyl, —NRC(O)alkynyl, —NRC(O)substituted alkynyl, —NRC(O)aryl, —NRC(O)substituted aryl, —NRC(O)heteroaryl, —NRC(O)substituted heteroaryl, —NRC(O)heterocyclic, and —NRC(O)substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the groups —NRC(O)O-alkyl, —NRC(O)O-substituted alkyl, —NRC(O)O-alkenyl, —NRC(O)O-substituted alkenyl, —NRC(O)O-alkynyl, —NRC(O)O-substituted alkynyl, —NRC(O)O-cycloalkyl, —NRC(O)O-substituted cycloalkyl, —NRC(O)O-aryl, —NRC(O)O-substituted aryl, —NRC(O)O-heteroaryl, —NRC(O)O-substituted heteroaryl, —NRC(O)O-heterocyclic, and —NRC(O)O-substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxycarbonylamino" refers to the groups —OC(O)NH₂, —OC(O)NRR, —OC(O)NR-alkyl, —OC(O)NR-substituted alkyl, —OC(O)NR-alkenyl, —OC(O)NR-substituted alkenyl, —OC(O)NR-alkynyl, —OC(O)NR-substituted alkynyl, —OC(O)NR-cycloalkyl, —OC(O)NR-substituted cycloalkyl, —OC(O)NR-aryl, —OC(O)NR-substituted aryl, —OC(O)NR-heteroaryl, —OC(O)NR-substituted heteroaryl, —OC(O)NR-heterocyclic, and —OC(O)NR-substituted heterocyclic where R is hydrogen, alkyl or where each R is joined to form, together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxythiocarbonylamino" refers to the groups —OC(S)NH₂, —OC(S)NRR, —OC(S)NR-alkyl, —OC(S)NR-substituted alkyl, —OC(S)NR-alkenyl, —OC(S)NR-substituted alkenyl, —OC(S)NR-alkynyl, —OC(S)NR-substituted alkynyl, —OC(S)NR-cycloalkyl, —OC(S)NR-substituted cycloalkyl, —OC(S)NR-aryl, —OC(S)NR-substituted aryl, —OC(S)NR-heteroaryl, —OC(S)NR-substituted heteroaryl, —OC(S)NR-heterocyclic, and —OC(S)NR-substituted heterocyclic where R is hydrogen, alkyl or where each R is joined to form together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the groups —NRC(O)NRR, —NRC(O)NR-alkyl, —NRC(O)NR-substituted alkyl, —NRC(O)NR-alkenyl, —NRC(O)NR-substituted alkenyl, —NRC(O)NR-alkynyl, —NRC(O)NR-substituted alkynyl, —NRC(O)NR-aryl, —NRC(O)NR-substituted aryl, —NRC(O)NR-cycloalkyl, —NRC(O)NR-substituted cycloalkyl, —NRC(O)NR-heteroaryl, and —NRC(O)NR-substituted heteroaryl, —NRC(O)NR-heterocyclic, and —NRC(O)NR-substituted heterocyclic where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the groups —NRC(S)NRR, —NRC(S)NR-alkyl, —NRC(S)NR-substituted alkyl, —NRC(S)NR-alkenyl, —NRC(S)NR-substituted alkenyl, —NRC(S)NR-alkynyl, —NRC(S)NR-substituted alkynyl, —NRC(S)NR-aryl, —NRC(S)NR-substituted aryl, —NRC(S)NR-cycloalkyl, —NRC(S)NR-substituted cycloalkyl, —NRC(S)NR-heteroaryl, and —NRC(S)NR-substituted heteroaryl, —NRC(S)NR-heterocyclic, and —NRC(S)NR-substituted heterocyclic where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" or "Ar" refers to a monovalent unsaturated aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7yl, and the like). Preferred aryls include phenyl and naphthyl. Substituted aryl refers to aryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituded aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetic di-substituted amines having different substituents selected from the group concisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or sustituted with —SO$_2$NRR where R is hydrogen or alkyl.

"Arylene" refers to a divalent unsaturated aromatic carbocyclic group of from 6 to 14 carbon atoms having a single ring (e.g., phenylene) or multiple condensed rings (e.g., naphthylene or anthrylene) which condensed rings may or may not be aromatic. Preferred arylenes include phenylene and naphtylene. Substituted arylene refers to arylene groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxylcycloalkly, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkly, guanidino, guanidinosulfone, halo, nitro heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$- substituted heterocyclic, —NRS(O)₂—NR-alkyl, —NRS(O)₂—NR-substituted alkyl, —NRS(O)₂—NR-aryl, —NRS(O)₂—NR-substituted aryl, —NRS(O)₂—NR-heteroaryl, —NRS(O)₂—NR-substituted heteroaryl, —NRS(O)₂—NR-heterocyclic, —NRS(O)₂—NR-substituted heterocyclic where R is hydrogen or alkyl, mono- and di-alkylamino, mono- and di-(substituted alkyl)amino, mono- and and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO₂NRR where R is hydrogen or alkyl.

"Aryloxy" refers to the group aryl-O—which includes, by way of example, phenoxy, naphthoxy, and the like.

"Substituted aryloxy" refers to substituted aryl-O— groups.

"Aryloxyaryl" refers to the group -aryl-O-aryl.

"Substituted aryloxyaryl" refers to aryloxyaryl groups substituted with from 1 to 3 substituents on either or both aryl rings selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)₂-alkyl, —S(O)₂-substituted alkyl, —S(O)₂-cycloalkyl, —S(O)₂-substituted cycloalkyl, —S(O)₂-alkenyl, —S(O)₂-substituted alkenyl, —S(O)₂-aryl, —S(O)₂-substituted aryl, —S(O)₂-heteroaryl, —S(O)₂-substituted heteroaryl, —S(O)₂-heterocyclic, —S(O)₂-substituted heterocyclic, —OS(O)₂-alkyl, —OS(O)₂-substituted alkyl, —OS(O)₂-aryl, —OS(O)₂-substituted aryl, —OS(O)₂-heteroaryl, —OS(O)₂-substituted heteroaryl, —OS(O)₂-heterocyclic, —OS(O)₂-substituted heterocyclic, —OSO₂—NRR where R is hydrogen or alkyl, —NRS(O)₂-alkyl, —NRS(O)₂-substituted alkyl, —NRS(O)₂-aryl, —NRS(O)₂-substituted aryl, —NRS(O)₂-heteroaryl, —NRS(O)₂-substituted heteroaryl, —NRS(O)₂-heterocyclic, —NRS(O)₂-substituted heterocyclic, —NRS(O)₂—NR-alkyl, —NRS(O)₂—NR-substituted alkyl, —NRS(O)₂—NR-aryl, —NRS(O)₂—NR-substituted aryl, —NRS(O)₂—NR-heteroaryl, —NRS(O)₂—NR-substituted heteroaryl, —NRS(O)₂—NR-heterocyclic, —NRS(O)₂—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO₂NRR where R is hydrogen or alkyl.

"Cycloalkyl" refers to cyclic alkyl groups of from 3 to 8 carbon atoms having a single cyclic ring including, by way of example, cyclopropyl, cyclobutyl, cyclopentyl, cyclooctyl and the like. Excluded from this definition are multi-ring alkyl groups such as adamantanyl, etc.

"Cycloalkyloxy" refers to —O-cycloalkyl.

"Cycloalkenyl" refers to cyclic alkenyl groups of frm 3 to 8 carbon atoms having a single cyclic ring.

"Cycloalkenyloxy" refers to —O-cycloalkenyl.

"Substituted cycloalkyl" and "substituted cycloalkenyl" refers to an cycloalkyl or cycloalkenyl group, preferably of from 3 to 8 carbon atoms, having from 1 to 5 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)₂-alkyl, —OS(O)₂-substituted alkyl, —OS(O)₂-aryl, —OS(O)₂-substituted aryl, —OS(O)₂-heteroaryl, —OS(O)₂-substituted heteroaryl, —OS(O)₂-heterocyclic, —OS(O)₂-substituted heterocyclic, —OSO₂—NRR where R is hydrogen or alkyl, —NRS(O)₂-alkyl, —NRS(O)₂-substituted alkyl, —NRS(O)₂-aryl, —NRS(O)₂-substituted aryl, —NRS(O)₂-heteroaryl, —NRS(O)₂-substituted heteroaryl, —NRS(O)₂-heterocyclic, —NRS(O)₂-substituted heterocyclic, —NRS(O)₂—NR-alkyl, —NRS(O)₂—NR-substituted alkyl, —NRS(O)₂—NR-aryl, —NRS(O)₂—NR-heteroaryl, —NRS(O)₂—NR-substituted heteroaryl, —NRS(O)₂—NR-heterocyclic, —NRS(O)₂—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Substituted cycloalkyloxy" and "substituted cycloalkenyloxy" refers to —O-substituted cycloalkyl and —O-substituted cycloalkenyloxy respectively.

"Cycloalkylene" refers to divalent cyclic alkylene groups of from 3 to 8 carbon atoms having a single cyclic ring including, by way of example, cyclopropylene, cyclobutylene, cyclopentylene, cyclooctylene and the like.

"Cycloalkenylene" refers to a divalent cyclic alkenylene groups of frm 3 to 8 carbon atoms having a single cyclic ring.

"Substituted cycloalkylene" and "substituted cycloalkenylene" refers to a cycloalkylene or cycloalkenylene group, preferably of from 3 to 8 carbon atoms, having from 1 to 5 substituents selected from the group consisting of oxo (═O), thioxo (═S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$—heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Cycloalkoxy" refers to —O-cycloalkyl groups.

"Substituted cycloalkoxy" refers to —O-substituted cycloalkyl groups.

"Guanidino" refers to the groups —NRC(═NR)NRR, —NRC(═NR)NR-alkyl, —NRC(═NR)NR-substituted alkyl, —NRC(═NR)NR-alkenyl, —NRC(═NR)NR-substituted alkenyl, —NRC(═NR)NR-alkynyl, —NRC(═NR)NR-substituted alkynyl, —NRC(═NR)NR-aryl, —NRC(═NR)NR-substituted aryl, —NRC(═NR)NR-cycloalkyl, —NRC(═NR)NR-heteroaryl, —NRC(═NR)NR-substituted heteroaryl, —NRC(═NR)NR-heterocyclic, and —NRC(═NR)NR-substituted heterocyclic where each R is independently hydrogen and alkyl as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"N,N-Dimethylcarbamyloxy" refers to the group —OC(O)N(CH$_3$)$_2$.

"Guanidinosulfone" refers to the groups —NRC(═NR)NRSO$_2$-alkyl, —NRC(═NR)NRSO$_2$-substituted alkyl, —NRC(═NR)NRSO$_2$-alkenyl, —NRC(═NR)NRSO$_2$-substituted alkenyl, —NRC(═NR)NRSO$_2$-alkynyl, —NRC(═NR)NRSO$_2$-substituted alkynyl, —NRC(═NR)NRSO$_2$-aryl, —NRC(═NR)NRSO$_2$-substituted aryl, —NRC(═NR)NRSO$_2$-cycloalkyl, —NRC(═NR)NRSO$_2$-substituted cycloalkyl, —NRC(═NR)NRSO$_2$-heteroaryl, and —NRC(═NR)NRSO$_2$-substituted heteroaryl, —NRC(═NR)NRSO$_2$-heterocyclic, and —NRC(═NR)NRSO$_2$-substituted heterocyclic where each R is independently hydrogen and alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Halo" or "halogen" refers to fluoro, chloro, bromo and iodo and preferably is either chloro or bromo.

"Heteroaryl" refers to an aromatic carbocyclic group of from 2 to 10 carbon atoms and 1 to 4 heteroatoms selected from the group consisting of oxygen, nitrogen and sulfur within the ring. Such heteroaryl groups can have a single ring (e.g., pyridyl or furyl) or multiple condensed rings (e.g., indolizinyl or benzothienyl). Preferred heteroaryls include pyridyl, pyrrolyl, indolyl and furyl.

"Substituted heteroaryl" refers to heteroaryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Heteroarylene" refers to a divalent aromatic carbocyclic group of from 2 to 10 carbon atoms and 1 to 4 heteroatoms selected from the group consisting of oxygen, nitrogen and sulfur within the ring. Such heteroarylene groups can have a single ring (e.g., pyridylene or furylene) or multiple condensed rings (e.g., indolizinylene or benzothienylene). Preferred heteroarylenes include pyridylene, pyrrolylene, indolylene and furylene.

"Substituted heteroarylene" refers to heteroarylene groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Heteroaryloxy" refers to the group —O-heteroaryl and "substituted heteroaryloxy" refers to the group —O-substituted heteroaryl.

"Heterocycle" or "heterocyclic" refers to a saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more the rings can be aryl or heteroaryl.

"Substituted heterocyclic" refers to heterocycle groups which are substituted with from 1 to 3 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, —C(O)O-aryl, —C(O)O-substituted aryl, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-hetero arylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

"Heterocyclene" refers to a divalent saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more the rings can be aryl or heteroaryl.

"Substituted heterocyclene" refers to heterocyclene groups which are substituted with from 1 to 3 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxylcycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, —C(O)O-aryl, —C(O)O-substituted aryl, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Heterocyclyloxy" refers to the group —O-heterocyclic and "substituted heterocyclyloxy" refers to the group —O-substituted heterocyclic.

"Thiol" refers to the group —SH.

"Thioalkyl" refers to the groups —S-alkyl

"Substituted thioalkyl" refers to the group —S-substituted alkyl.

"Thiocycloalkyl" refers to the groups —S-cycloalkyl.

"Substituted thiocycloalkyl" refers to the group —S-substituted cycloalkyl.

"Thioaryl" refers to the group —S-aryl and "substituted thioaryl" refers to the group —S-substituted aryl.

"Thioheteroaryl" refers to the group —S-heteroaryl and "substituted thioheteroaryl" refers to the group —S-substituted heteroaryl.

"Thioheterocyclic" refers to the group —S-heterocyclic and "substituted thioheterocyclic" refers to the group —S-substituted heterocyclic.

"Amino" refers to the —NH$_2$ group.

"Substituted amino" refers to the —NR'R" group wherein R' and R" are independently hydrogen, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, heterocyclic, substituted heterocyclic or where R' and R", together with the nitrogen atom pendent thereto, form a heterocyclic ring.

"Pharmaceutically acceptable salt" refers to pharmaceutically acceptable salts of a compound of Formulae (I), which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

Utility

The compounds and methods described herein provide for the sustained release of drugs or active metabolites thereof relative to dosing with the parent drug itself. In this regard, enterohepatic recycling of the bile acid conjugates creates a reservoir for the active agent.

General Synthetic Scheme

Compounds of this invention can be made by the methods depicted in the reaction schemes shown below.

The starting materials and reagents used in preparing these compounds are either available from commercial suppliers such as Aldrich Chemical Co., (Milwaukee, Wis., USA), Bachem (Torrance, Calif., USA), Emka-Chemie, or Sigma (St. Louis, Mo., USA) or are prepared by methods known to those skilled in the art following procedures set forth in references such as Fieser and Fieser's Reagents for Organic Synthesis, Volumes 1–15 (John Wiley and Sons, 1991); Rodd's Chemistry of Carbon Compounds, Volumes 1–5 and Supplementals (Elsevier Science Publishers, 1989), Organic Reactions, Volumes 1–40 (John Wiley and Sons, 1991), March's Advanced Organic Chemistry, (John Wiley and Sons, 4th Edition), and Larock's Comprehensive Organic Transformations (VCH Publishers Inc., 1989).

These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Preparation of Compounds of Formula (I)

Schemes A and B describe alternative methods to prepare the compounds of Formula (I).

Compounds of formula (I-1) where X, R$^1$ and R$^2$ are hydroxy, Z is a substituted alkyl group containing a group of the formula —M-Q$^{x'}$, M is —CH$_2$CH$_2$C(O)—, Q$^{x'}$ is of the structure —A$^{x'}$-D', A$^{x'}$ is derived from an α-amino acid, and D' is a drug of formula (b):

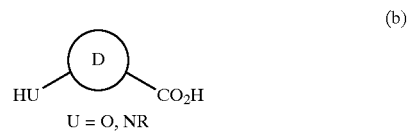

can be prepared as illustrated and described in Scheme A below.

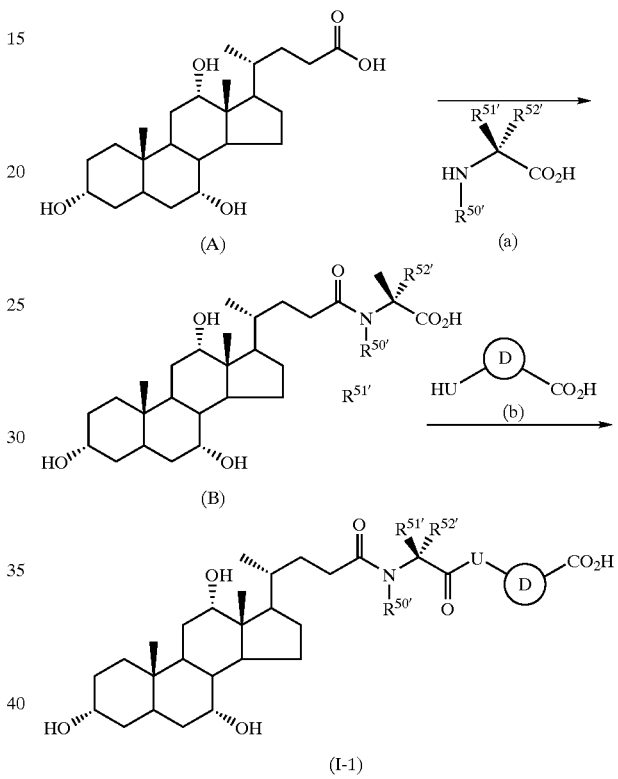

In reference to Scheme A, commercially available cholic acid (A) is treated with an activating agent, such as ethylchloroformate in the presence of diisopropylethylamine, to provide an activated anhydride. The activated anhydride is reacted with amino acid (a) forming acid (B). Activation of (B) using an activating agent and condensation with drug (b) affords a compound of formula (I-1) as shown.

One of ordinary skill in the art will appreciate that cholic acid (A) could alternatively be reacted with amino acid (a) in the presence of a coupling agent (e.g., dicyclohexylcarbodiimide) to provide acid (B). Alternatively, cholic acid (A) could be coupled with the dipeptide (or depsipeptide) resulting from first coupling amino acid (a) to compound (b).

A compound of formula (I-2) where R$^1$ and R$^2$ are hydroxy, Z is —CH$_2$CH$_2$CO$_2$H, X is Q$^x$-G-, G is —O—, Q$^x$ is -D-A$^x$, A$^x$ is derived from an α-amino acid, and D is a drug of formula (b):

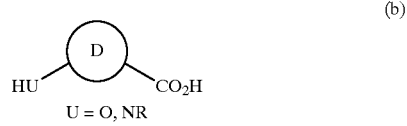

can be prepared as illustrated and described in Scheme B below.

Scheme B

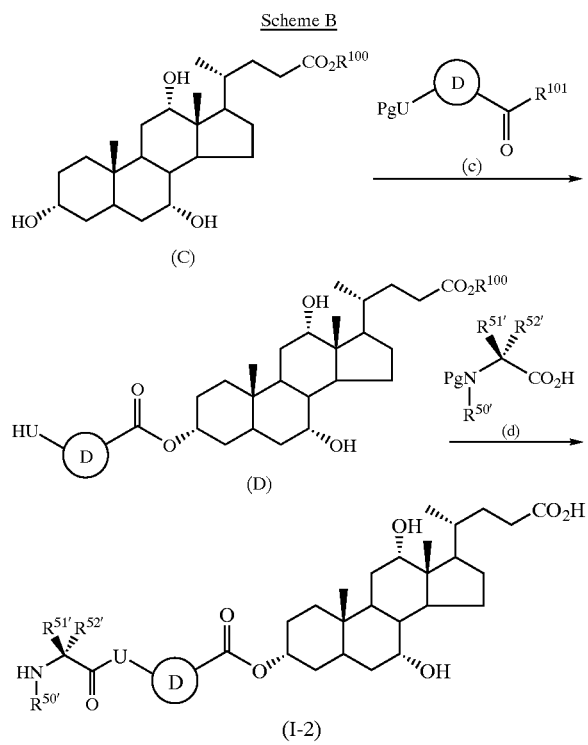

In reference to Scheme B, compound (C), wherein $R^{100}$ is a carboxyl protecting group, is coupled with activated acid derivative (c), wherein $R^{101}$ is a suitable leaving group (e.g., —OC(O)OEt). Selective deprotection of the amino or hydroxyl protecting group (i.e., Pg) provides compound (D). Activation of carboxylic acid (d) (e.g., treatment with ethyl chloroformate in the presence of a tertiary amine) followed by addition to (D) then removal of protecting groups yields the desired compound of formula (I-2).

One of ordinary skill in the art will appreciate that one could also use a coupling agent (e.g. a carbodiimide) in situ to form the amide or ester bonds above (i.e., bond between (C) and (c) or between (D) and (d)) rather than condensing a preformed activated acid derivative (i.e., (c) or (d)).

Analogous synthetic methods can be used in the preparation of compounds of formula (II) and (III).

Figure 5:
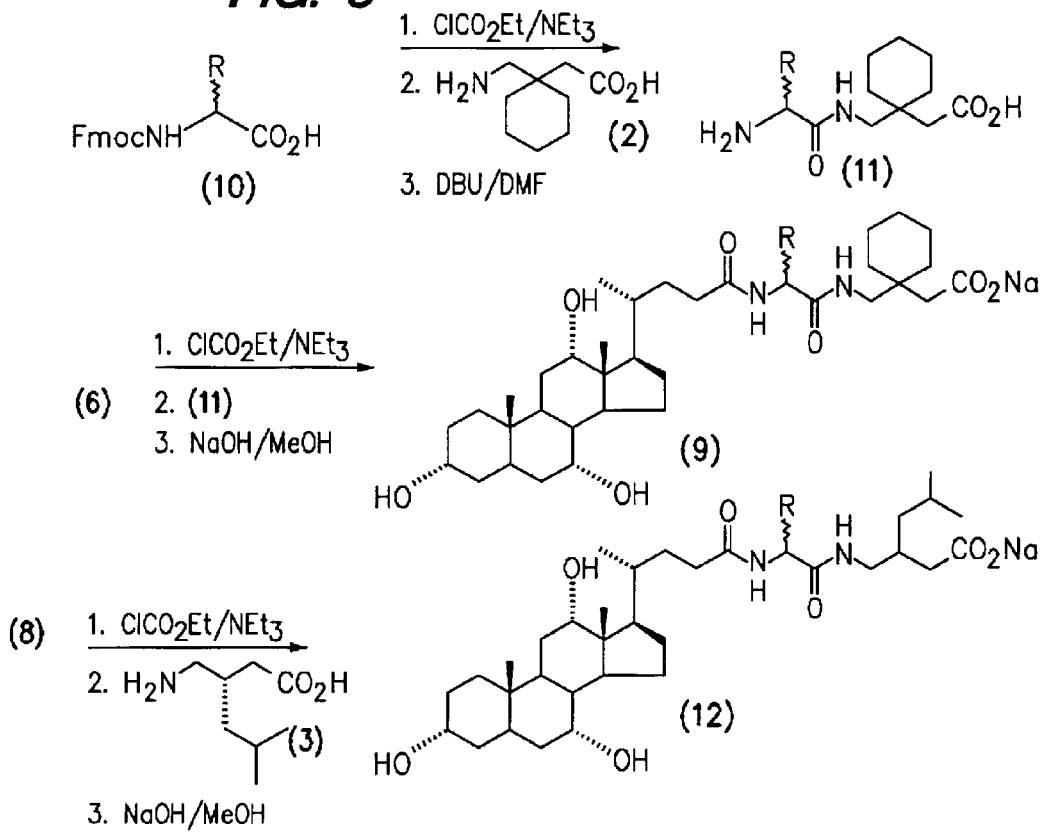
Figure 6:
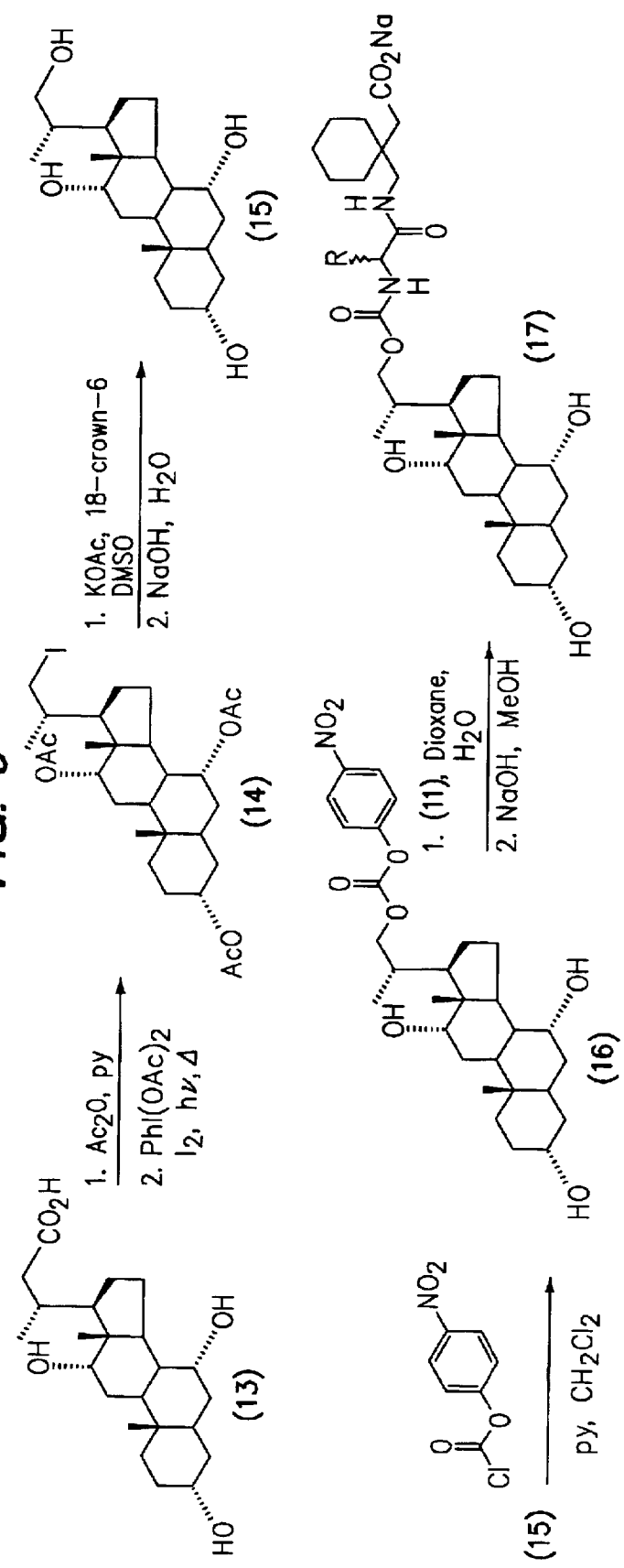

Additionally, FIGS. 4–8 and Examples 1–8 below describe in detail the synthesis and biological activity of various bile acid-derived compounds.

Pharmaceutical Formulations

When employed as pharmaceuticals, the compounds of formula (I), (II) or (III) are usually administered in the form of pharmaceutical compositions. These compounds can be administered by a variety of routes including oral, rectal, subcutaneous, intravenous, intramuscular and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds of formula (I) above associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.1 to about 5000 mg, more usually about 10 to about 2000 mg, of the active ingredient. The term "unit dosage forms" refers to physically discrete units suitable as unitary dosages for human subjects and other animals, each unit containing a predetermined quantity of active material calculated to produce the desired therapeutic effect, in association with a suitable pharmaceutical excipient.

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 mg to about 2 g of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner.

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

| | |
|---|---|
| Atm = | atmosphere |
| Boc = | tert-butyloxycarbonyl |
| Cbz = | carbobenzyloxy |
| CPM = | counts per minute |
| DIC = | diisopropylcarbodiimide |
| DMAP = | 4-N,N-dimethylaminopyridine |
| DMEM = | Dulbecco's minimun eagle medium |
| DMF = | N,N-dimethylformamide |
| DMSO = | dimethylsulfoxide |
| FMOC = | 9-fluorenylmethyloxycarbonyl |
| g = | gram |
| h = | hour |
| HBSS = | Hank's buffered saline solution |
| IBAT = | intestinal bile acid transporter |
| L = | liter |
| LBAT = | liver bile acid transporter |
| LC/MS = | liquid chromatography/mass spectroscopy |
| M = | molar |
| min = | minute |

-continued

| | |
|---|---|
| mL = | milliliter |
| mmol = | millimols |
| NTCP = | Na+ taurocholate cotransporting polypeptide |
| PBS = | phosphate buffered saline |
| PPTS = | pyridinium p-toluenesulfonate |
| THF = | tetrahydrofuran |
| TFA = | trifluoroacetic acid |
| TMSOTf = | trimethylsilyltrifluoromethanesulfonate |
| Trisyl = | 2,4,6-triisopropylbenzenesulfonyl |
| $\mu$L = | microliter |
| $\mu$M = | micromolar |
| v/v = | volume to volume |

Experimental Methods

The following examples illustrate how the synthesis of GABA analog conjugates could be conducted in order to prepare compounds of formula (I). It is contemplated that other drugs may be used in place of a GABA analog with similar synthetic schemes. The syntheses described below are illustrated in FIG. 4–8. While GABA is not included within the scope of this invention, these examples are illustrative of how other drugs could be readily coupled to a bile acid in an analogous manner.

Example 1

Synthesis of Cholic Acid Gabapentin Dipeptides (9)

Cholic acid (6) (408 mg, 1 mmol) was dissolved in anhydrous THF (10 mL) and triethylamine (0.167 mL, 1.2 mmol) added slowly with stirring. The solution was cooled to −5° C. in an ice-salt bath, and ethyl chloroformate (0.12 mL, 1.2 mmol) added slowly, maintaining the temperature between −5 to 0° C. After addition was complete, the cold mixture was stirred for an additional 15 minutes. A solution containing an amino acid (7) (1.75 mmol) in 2N NaOH (2 mL) was added and the mixture stirred for an additional 60 min at −5 to 0° C. After removal of the THF in vacuo, saturated NaHCO$_3$ (15 mL) was added and the aqueous mixture washed with EtOAc (3×10 mL), then the pH adjusted to 3–4 with citric acid. The product was extracted into EtOAc (3×15 mL), and the combined organic phase dried over MgSO$_4$, and concentrated to dryness. The residue was purified by flash chromatography on silica gel (5% MeOH/CH$_2$Cl$_2$) to give the pure cholic acid adduct (8). This compound (0.4 mmol) was dissolved in anhydrous THF (10 mL) and triethylamine (0.44 mmol) added slowly with stirring. The solution was cooled to −5° C. in an ice-salt bath, and ethyl chloroformate (44 $\mu$L, 0.44 mmol) added slowly, maintaining the temperature between −5 to 0° C. After addition was complete, the cold mixture was stirred for an additional 15 minutes. A solution containing gabapentin (2) (166 mg, 0.8 mmol) in 2N NaOH (3 mL) was added and the mixture stirred for an additional 60 min at −5 to 0° C. After removal of the THF in vacuo, saturated NaHCO$_3$ (10 mL) was added and the aqueous mixture washed with EtOAc (3×10 mL), then the pH adjusted to 3–4 with citric acid. The product was extracted into EtOAc (3×20 mL), and the combined organic phases dried over MgSO$_4$, and concentrated to dryness. The residue was purified by flash chromatography on silica gel (10% MeOH/CH$_2$Cl$_2$) to give the pure cholic acid gabapentin dipeptide derivative. The corresponding sodium salt (9) was prepared in quantitative yield by addition of a methanol solution of the acid to water containing 0.5N NaOH (1 eq.) and evaporation to dryness on a lyophilizer. Compounds were characterized by electrospray mass spectrometry as reported below:

Cholyl-Gly-Gabapentin (9a): MS (ESI): m/z 617.50 (M−H⁻), 619.51 (M+H⁺). ¹H NMR (CD₃OD, 400 MHz, characteristic resonances only): 3.81 (s, 2H), 3.34 (s, 2H), 2.28 (s, 2H), 1.03 (d, 3H, J=6.4 Hz), 0.91 (s, 3H), 0.70 (s, 3H).

Cholyl-Ala-Gabapentin (9b): MS (ESI): m/z 631.50 (M−H⁻), 633.52 (M+H⁺). ¹H NMR (CD₃OD, 400 MHz, characteristic resonances only): 4.29 (m, 1H), 3.34 (s, 2H), 2.28 (s, 2H), 1.34 (d, 2H, J=6.8 Hz), 1.01 (d, 3H, J=6.4 Hz), 0.91 (s, 3H), 0.71 (s, 3H).

Cholyl-Val-Gabapentin (9c): MS (ESI): m/z 659.55 (M−H⁻), 661.55 (M+H⁺). ¹H NMR (CD₃OD, 400 MHz, characteristic resonances only): 4.26 (m, 1H), 3.34 (s, 2H), 2.27 (s, 2H), 1.02 (d, 3H, J=6.4 Hz), 0.97 (d, 6H, J=6.4 Hz), 0.91 (s, 3H), 0.71 (s, 3H).

Cholyl-Leu-Gabapentin (9d): MS (ESI): m/z 673.43 (M−H⁻), 675.45 (M+H⁺). ¹H NMR (CD₃OD, 400 MHz, characteristic resonances only): 4.34 (m, 1H), 3.34 (s, 2H), 2.27 (s, 2H), 1.02 (d, 3H, J=6.4 Hz), 0.97 (d, 3H, J=6.4 Hz), 0.92 (d, 3H, J=6.4 Hz), 0.91 (s, 3H), 0.70 (s, 3H).

Cholyl-Norleu-Gabapentin (9e): MS (ESI): m/z 659.56 (M−H⁻), 661.57 (M+H⁺). ¹H NMR (CD₃OD, 400 MHz, characteristic resonances only): 4.26 (m, 1H), 3.34 (s, 2H), 2.27 (s, 2H), 1.02 (d, 3H, J=6.4 Hz), 0.91 (s, 3H), 0.71 (s, 3H).

Cholyl-BuGly-Gabapentin (9f): MS (ESI): m/z 673.58 (M−H⁻), 675.58 (M+H⁺). ¹H NMR (CD₃OD, 400 MHz, characteristic resonances only): 4.20 (s, 1H), 3.34 (s, 2H), 2.29 (s, 2H), 1.01 (d, 3H, J=6.4 Hz), 0.98 (s, 9H), 0.91 (s, 3H), 0.70 (s, 3H).

Cholyl-Phe-Gabapentin (9g): MS (ESI): m/z 707.47 (M−H⁻), 709.36 (M+H⁺). ¹H NMR (CD₃OD, 400 MHz, characteristic resonances only): 7.26 (m, 5H), 4.59 (m, 1H), 3.34 (s, 2H), 3.25–2.95 (m, 2H), 2.18 (d, 2H, J=7.2 Hz), 0.98 (d, 3H, J=6.4 Hz), 0.91 (s, 3H), 0.68 (s, 3H).

Cholyl-Tyr-Gabapentin (9h): MS (ESI): m/z 723.42 (M−H⁻), 725.42 (M+H⁺). ¹H NMR (CD₃OD, 400 MHz, characteristic resonances only): 7.06 (d, 2H, J=8.8 Hz), 6.69 (d, 2H, J=8.8 Hz), 4.51 (dd,1H, J=6.8 Hz, J=8.8 Hz), 3.34 (s, 2H), 3.16–2.78 (m, 2H), 2.16 (d, 2H, J=7.2 Hz), 0.98 (d, 3H, J=6.4 Hz), 091 (s, 3H), 0.68 (s, 3H).

Cholyl-Ser-Gabapentin (9i): MS (ESI): m/z 647.42 (M−H⁻), 649.41 (M+H⁺). ¹H NMR (CD₃OD, 400 MHz, characteristic resonances only): 4.37 (m, 1H), 3.78 (m, 2H), 3.34 (s, 2H), 2.15 (s, 2H), 1.03 (d, 3H, J=6.4 Hz), 0.91 (s, 3H), 0.71 (s, 3H).

Cholyl-Asp-Gabapentin (9j): MS (ESI): m/z 647.45 (M−H⁻), 649.45 (M+H⁺). ¹H NMR (CD₃OD, 400 MHz, characteristic resonances only): 4.71 (m, 1H), 3.34 (s, 2H), 2.87–2.65 (m, 2H), 2.28 (s, 2H), 1.02 (d, 3H, J=6.4 Hz), 0.91 (s, 3H), 0.71 (s, 3H).

Cholyl-Glu-Gabapentin (9k): MS (ESI): m/z 688.50 (M−H⁻), 690.54 (M+H⁺). ¹H NMR (CD₃OD, 400 MHz, characteristic resonances only): 4.35 (m, 1H), 3.34 (s, 2H), 2.38 (t, 2H, J=7 Hz), 1.02 (d, 3H, J=6.4 Hz), 0.91 (s, 3H), 0.71 (s, 3H).

Cholyl-Asn-Gabapentin (9l): MS (ESI): m/z 674.43 (M−H³¹), 676.44 (M+H⁺). ¹H NMR (CD₃OD, 400 MHz, characteristic resonances only): 4.29 (m, 1H), 3.34 (s, 2H), 2.92–2.69 (m, 2H), 2.28 (s, 2H), 1.02 (d, 3H, J=6.4 Hz), 0.91 (s, 3H), 0.70 (s, 3H).

Cholyl-Lys-Gabapentin (9m): MS (ESI): m/z 688.50 (M−H⁻), 690.54 (M+H⁺). ¹H NMR (CD₃OD, 400 MHz, characteristic resonances only): 4.29 (m, 1H), 3.34 (s, 2H), 2.28 (s, 2H), 1.02 (d, 3H, J=6.4 Hz), 0.91 (s, 3H), 0.70 (s, 3H).

Cholyl-β-Ala-Gabapentin (9n): MS (ESI): m/z 631.45 (M−H⁻), 633.45 (M+H⁺). ¹H NMR (CD₃OD, 400 MHz, characteristic resonances only): 3.34 (s, 2H), 3.20 (t, 2H, J=8 Hz), 2.29 (s, 2H), 2.26 (t, 2H, J=8 Hz), 1.02 (d, 3H J=6.4 Hz), 0.91 (s, 3H), 0.70 (s, 3H).

Cholyl-Gaba-Gabapentin (9o): MS (ESI): m/z 645.56 (M−H⁻), 647.57 (M+H⁺). ¹H NMR (CD₃OD, 400 MHz, characteristic resonances only): 3.34 (s, 2H), 3.41 (t, 2H, J=6.8 Hz), 2.44 (t, 2H, J=6.8 Hz), 2.28 (s, 2H), 1.01 (d, 3H, J=6.4 Hz), 0.91 (s, 3H), 0.71 (s, 3H).

Ursodeoxycholyl-Phe-Gabapentin (9p): MS (ESI) m/z 691.6 (M−H⁻), 693.5 (M+H⁺). ¹H NMR (CD₃OD, 400 MHz, characteristic resonances only): 7.26 (m, 5H), 4.60 (m,1H), 3.34 (s, 2H), 3.25–2.95 (m, 2H), 2.08 (d, 2H, J=7 Hz), 0.95 (s, 3H), 0.91 (d, 3H, J=6.4 Hz), 0.67 (s, 3H).

Alternative Synthesis of Cholic Acid Gabapentin Dipeptides (9)

An N-Fmoc-protected amino acid (10) (1 mmol) is dissolved in anhydrous THF (10 mL) and triethylamine (0.167 mL, 1.2 mmol) added slowly with stirring. The solution is cooled to −5° C. in an ice-salt bath, and ethyl chloroformate (0.12 mL, 1.2 mmol) added slowly, maintaining the temperature between −5 to 0° C. After addition is complete, the cold mixture is stirred for an additional 15 minutes. A solution containing gabapentin (2) (1.75 mmol) in 2N NaOH (2 mL) is added and the mixture stirred for an additional 60 min at −5 to 0° C. After removal of the THF in vacuo, saturated NaHCO₃ (15 mL) is added and the aqueous mixture washed with EtOAc (3×10 mL), then the pH adjusted to 3–4 with citric acid. The product is extracted into EtOAc (3×15 mL), and the combined organic phase dried over MgSO₄, and concentrated to dryness. The residue is purified by flash chromatography on silica gel (5% MeOH/CH₂Cl₂) to give the pure protected dipeptide adduct. This compound is dissolved in dry NMP (4 mL) containing 5% (v/v) DBU and the solution stirred for 30 min to give the dipeptide (11). Cholic acid (6) (1 mmol) is dissolved in anhydrous THF (10 mL) and triethylamine (0.167 mL, 1.2 mmol) added slowly with stirring. The solution is cooled to −5° C. in an ice-salt bath, and ethyl chloroformate (0.12 mL, 1.2 mmol) added slowly, maintaining the temperature between −5 to 0° C. After addition is complete, the cold mixture is stirred for an additional 15 minutes. The above solution of dipeptide (11) is added and the mixture stirred for an additional 60 min at −5 to 0° C. After removal of the solvent in vacuo, saturated NaHCO₃ (15 mL) is added and the aqueous mixture washed with EtOAc (3×10 mL), then the pH adjusted to 3–4 with citric acid. The product is extracted into EtOAc (3×15 mL), and the combined organic phase dried over MgSO₄, and concentrated to dryness. The residue is purified by flash chromatography on silica gel (10% MeOH/CH₂Cl₂) to give the pure cholic acid gabapentin dipeptide derivative. The corresponding sodium salt (9) is prepared in quantitative yield by addition of a methanol solution of the acid to water containing 0.5N NaOH (1 eq.) and evaporation to dryness on a lyophilizer.

Example 2

Synthesis of Cholic Acid Pregabalin Dipeptides (12)

Pregabalin (3), prepared according the methods described in Silverman et al (U.S. Pat. No. 5,563,175), is transformed to the cholyl dipeptide derivative (12) following the procedure detailed above for the gabapentin analog (9).

Example 3

In Vitro Compound Transport Assays with IBAT and LBAT-Expressing Cell Lines (a) Inhibition of Radiolabeled Taurocholate Uptake CHO cells transfected with the IBAT or LBAT transporter were seeded into 96-well microtiter plates at 100,000 cells/well in 100 μL DMEM containing 10% serum, glutamine and Penstrep. After overnight incubation the media was removed and test compound (25 μL) added at 2× the final desired concentration. Tritiated taurocholate (50,000 CPM/well) was diluted with cold substrate to a final concentration of 5 μM and 25 μL/well of this mixture was added to the plate. After incubating for 1 h at room temperature the solution was removed and the plate washed 4× with PBS at 4° C. 200 μL/well of scintillant is added and the plate then read in a Wallac microbeta counter. The inhibition data is processed by standard methods to calculate an inhibition constant $K_i$ for the test compound.

(b) Analysis of Electrogenic Transport in Xenopus Oocytes

RNA preparation: Human IBAT Transporter cDNAs were subcloned into a modified pGEM plasmid that contains 5' and 3' untranslated sequences from the *Xenopus* β-actin gene. These sequences increase RNA stability and protein expression. Plasmid cDNA was linearized and used as template for in vitro transcription (Epicentre Technologies transcription kit, 4:1 methylated:non-methylated GTP).

*Xenopus* oocyte isolation. *Xenopus laevis* frogs were anesthetized by immersion in Tricaine (1.5 g/mL in deionized water) for 15 min. Oocytes were removed and digested in frog ringer solution (90 mM NaCl, 2 mM KCl, 1 mM $MgCl_2$, 10 mM NaHEPES, pH 7.45, no $CaCl_2$) with 1 mg/mL collagenase (Worthington Type 3) for 80–100 min with shaking. The oocytes were washed 6 times, and the buffer changed to frog ringer solution containing $CaCl_2$ (1.8 mM). Remaining follicle cells were removed if necessary. Cells were incubated at 16° C., and each oocyte injected with 10–20 μg RNA in 45 μL solution.

Electrophysiology measurements. Transport currents were measured 2–14 days after injection, using a standard two-electrode electrophysiology set-up (Geneclamp 500 amplifier, Digidata 1320/PCLAMP software and ADInstruments hardware and software were used for signal acquisition). Electrodes (2–4 mΩ) were microfabricated using a Sutter Instrument puller and filled with 3M KCl. The bath was directly grounded (transporter currents were less than 0.3 μA). Bath flow was controlled by an automated perfusion system (ALA Scientific Instruments, solenoid valves).

For transporter pharmacology, oocytes were clamped at −60 to −90 mV, and continuous current measurements acquired using PowerLab Software and an ADInstruments digitizer. Current signals were lowpass filtered at 20 Hz and acquired at 4–8 Hz. All bath and drug-containing solutions were frog ringers solution containing $CaCl_2$. Drugs were applied for 10–30 seconds until the induced current reached a new steady-state level, followed by a control solution until baseline currents returned to levels that preceded drug application. The difference current (baseline subtracted from peak current during drug application) reflected the net movement of charge resulting from electrogenic transport and was directly proportional to tranport rate. Recordings were made from a single oocyte for up to 60 min, enabling 30–40 separate compounds to be tested per oocyte. Compound-induced currents were saturable and gave half-maximal values at substrate concentrations comparable to radiolabel competition experiments. To compare results between oocytes expressing different levels of transport activity, a saturating concentration of glycodeoxycholate (300 μM) was used as a common reference to normalize results from test compounds. Using this normalization procedure $V_{max}$ (i.e. maximal induced current) for different compounds tested on different oocytes could be compared.

TABLE 1

In vitro transport data for selected compounds on IBAT-expressing cells

| COMPOUND | $IC_{50}$ (μM) | $EC_{50}$ (μM) | % Max. (GDC) |
|---|---|---|---|
| Cholyl-Gly-Gabapentin (9a) | 66 | 22 | 67 |
| Cholyl-Phe-Gabapentin (9g) | 92 | 140 | 28 |
| Cholyl-Tyr-Gabapentin (9h) | 52 | 160 | 13 |
| UDC-Phe-Gabapentin (9p) | 27 | 18 | 27 |

$IC_{50}$ data from radiolabeled competition assay in transporter-expressing CHO cells
$EC_{50}$ and % Max data (relative to glycodeoxycholate) from transporter-expressing oocytes

TABLE 2

In vitro transport data for selected compounds on LBAT-expressing cells

| COMPOUND | $IC_{50}$ (μM) | $EC_{50}$ (μM) | % Max. (GDC) |
|---|---|---|---|
| Cholyl-Gly-Gabapentin (9a) | 64 | ND | ND |
| Cholyl-Phe-Gabapentin (9g) | 0.5 | ND | ND |
| Cholyl-Tyr-Gabapentin (9h) | 15 | ND | ND |
| UDC-Phe-Gabapentin (9p) | 0.7 | ND | ND |

$IC_{50}$ data from radiolabeled competition assay in transporter-expressing CHO cells
$EC_{50}$ and % Max data (relative to glycodeoxycholate) from transporter-expressing oocytes

Example 4

In Vitro Compound Transport Assays with PEPT1 and PEPT2-Expressing Cell Lines-Inhibition of Radiolabeled Gly-Sar Uptake Rat and human PEPT1 and PEPT2 expressing CHO cell lines were prepared as described in PCT Application WO01/20331. Gabapentin-containing dipeptides were evaluated for interaction with the peptide transporters using a radiolabeled substrate uptake assay in a competitive inhibition format, as described in PCT Application WO01/20331. Transport-induced currents were also measured in *Xenopus* oocytes transfected with rat and human PEPT1 and PEPT2.

TABLE 3

In vitro transport data for selected compounds on rPEPT1-expressing cells

| COMPOUND | $IC_{50}$ (μM) | % Max. (Gly-Sar) |
|---|---|---|
| Gly-Gabapentin | 320 | 76 |
| Phe-Gabapentin | 56 | 52 |
| Tyr-Gabapentin | 130 | 22 |

$IC_{50}$ data from radiolabeled competition assay in transporter-expressing CHO cells
% Max response (relative to Gly-Sar) from transporter-expressing oocytes at a test compound concentration of 1 mM

TABLE 4

In vitro transport data for selected compounds on rPEPT2-expressing cells

| COMPOUND | $IC_{50}$ ($\mu$M) | % Max. (Gly-Sar) |
|---|---|---|
| Gly-Gabapentin | ND | ND |
| Phe-Gabapentin | ND | 77 |
| Tyr-Gabapentin | 4 | 73 |

$IC_{50}$ data from radiolabeled competition assay in transporter-expressing CHO cells
% Max response (relative to Gly-Sar) from transporter-expressing oocytes at a test compound concentration of 1 mM

Example 5

In Vitro Enzymatic Release of Gabapentin from Cholyl-Amino Acid-Gabapentin Conjugates Sustained oral delivery of a drug molecule by attachment through a cleavable linker arm to an actively transported promoiety requires that the drug eventually be released from the drug/cleavable linker/transporter compound (prodrug) by enzymatic cleavage in one or more tissues of the enterohepatic circulation. The release of Gabapentin from the prodrug Cholyl-Phe-Gabapentin (9 g) (and other Cholyl-Amino Acid-Gabapentin conjugates (9)) was evaluated in vitro using tissues representative of those involved in the enterohepatic circulation. These studies indicated that in vitro cleavage of the prodrug could occur via a stepwise process, with release of the Gabapentin-containing dipeptide (e.g. Phe-Gabapentin) preceeding hydrolysis to liberate free Gabapentin.

Tissues were obtained from commercial sources (e.g., Pel-Freez Biologicals, Rogers, Ark., or GenTest Corporation, Woburn, Mass.). Stability of Cholyl-Phe-Gabapentin towards specific enzymes (e.g., carboxypeptidase A, cholylglycine hydrolase) was also evaluated by incubation with the purified enzyme.

Experimental conditions used for the in vitro studies are described in Table 3 below. Each preparation was incubated with (9 g) at 37° C. for one hour. Aliquots (50 $\mu$L) were removed at 0, 30, and 60 min and quenched with 0.1% trifluoroacetic acid in acetonitrile. Samples were then centrifuged and analyzed by LC/MS/MS as described below.

The stability of Gabapentin-containing dipeptides to purified aminopeptidase 1 and to Caco-2 homogenates was evaluated as follows:

Aminopeptidase Stability: Aminopeptidase 1 (Sigma catalog # A-9934) was diluted in deionised water to a concentration of 856 units/mL. Stability studies were conducted by incubating prodrug (5 $\mu$M) with 0.856 units/mL aminopeptidase 1 in 50 mM Tris-HCl buffer at pH 8.0 and 37° C. Concentrations of intact prodrug and released drug were determined at zero time and 60 minutes using LC/MS/MS.

Pancreatin Stability: Stability studies were conducted by incubating prodrug (5 $\mu$M) with 1% (w/v) pancreatin (Sigma, P-1 625, from porcine pancreas) in 0.025 M Tris buffer containing 0.5 M NaCl (pH 7.5) at 37 ° C. for 60 min. The reaction was stopped by addition of 2 volumes of methanol. After centrifugation at 14,000 rpm for 10 min, the supernatant was removed and analyzed by LC/MS/MS.

Caco-2 Homogenate S9 Stability: Caco-2 cells were grown for 21 days prior to harvesting. Culture medium was removed and cell monolayers were rinsed and scraped off into ice-cold 10 mM sodium phosphate/0.15 M potassium chloride, pH 7.4. Cells were lysed by sonication at 4° C. using a probe sonicator. Lysed cells were then transferred into 1.5 mL centrifuge vials and centrifuged at 9000 g for 20 min at 4° C. The resulting supernatant (Caco-2 cell homogenate S9 fraction) was aliquoted into 0.5 mL vials and stored at −80° C. until used. For stability studies, prodrug (5 $\mu$M) was incubated in Caco-2 homogenate S9 fraction (0.5 mg protein per mL) for 60 min at 37° C. Concentrations of intact prodrug and released drug were determined at zero time and 60 minutes using LC/MS/MS.

Concentrations of Cholyl-Phe-Gabapentin (9g), Phe-Gabapentin or Gabapentin in tissue extracts were determined by direct injection onto an API 2000 LC/MS/MS equipped with an Agilent 1100 binary pump and autosampler. Separation was achieved using a 3.5 $\mu$m Zorbax Ellipse XDB-C8 4.4×150 mm column heated to 45° C. during the analysis. The mobile phases were: 0.1% formic acid in water (A) and 0.1% formic acid in acetonitrile (B). The gradient condition was: 2% B for 0.5 min, increasing to 90% B in 2.0 min, maintained for 2.5 min and returning to 2% B for 2 min. A TurboIonSpray source was used on the API 2000. The analysis was performed in the positive ion mode and MRM transitions of 709.5/172.1 and 172.0/137.2 were used in the analysis of Cholyl-Phe-Gabapentin Phe-Gabapentin (9 g) and Gabapentin (2) respectively. Ten microliters of the sample extracts were injected. Peaks were integrated using Analyst quantitation software. The method was linear for (9 g) or (2) over the concentration range 0.01 to 12.5 $\mu$g/mL and 0.002 to 2.5 $\mu$g/mL respectively.

TABLE 5

In Vitro Enzymatic Release of Phe-Gabapentin from Cholyl-Phe-Gabapentin (9g)

| Preparation | Substrate Concentration | Cofactors | Percent of Phe-Gabapentin Released in 60 min |
|---|---|---|---|
| Rat Plasma | 2.0 $\mu$M | None | NR |
| Human Plasma | 2.0 $\mu$M | None | NR |
| Rat Liver S9 (0.5 mg/mL) | 2.0 $\mu$M | NADPH | NR |
| Human Liver S9 (0.5 mg/mL) | 2.0 $\mu$M | NADPH | NR |
| Human Intestine S9 (0.5 mg/mL) | 2.0 $\mu$M | NADPH | NR |
| Cholylglycine Hydrolase (87 units/mL) | 0.8 $\mu$M | None | ~3 |
| Carboxypeptidase A (10 units/mL) | 2.0 $\mu$M | None | NR |

NR = Not released

TABLE 6

In Vitro Enzymatic Release of Gabapentin (2) from Phe-Gabapentin

| Preparation | Substrate Concentration | Cofactors | Percent of Gabapentin Released in 60 min |
|---|---|---|---|
| Rat Plasma | 2.0 $\mu$M | None | 19 |
| Human Plasma | 2.0 $\mu$M | None | NR |
| Rat Liver S9 (0.5 mg/mL) | 2.0 $\mu$M | NADPH | 1 |

TABLE 6-continued

In Vitro Enzymatic Release of Gabapentin (2) from Phe-Gabapentin

| Preparation | Substrate Concentration | Cofactors | Percent of Gabapentin Released in 60 min |
|---|---|---|---|
| Human Liver S9 (0.5 mg/mL) | 2.0 µM | NADPH | 1 |
| Human Intestine S9 (0.5 mg/mL) | 2.0 µM | NADPH | 5 |
| Cholylglycine Hydrolase (87 units/mL) | 0.8 µM | None | NR |
| Carboxypeptidase A (10 units/mL) | 2.0 µM | None | NR |
| Caco-2 Homogenate | 5.0 µM | None | 21 |
| Aminopeptidase | 5.0 µM | None | 24 |

NR = Not released

TABLE 7

In Vitro Enzymatic Release of Gabapentin (2) from Cholyl-Amino Acid-Gabapentin Compounds by Pancreatin

| COMPOUND | % (2) Released |
|---|---|
| Cholyl-Gly-Gabapentin (9a) | NR |
| Cholyl-Phe-Gabapentin (9g) | 4 |
| Cholyl-Tyr-Gabapentin (9h) | 40 |

NR = Not released

Example 6

Sustained Release of Gabapentin (2) from Cholvl-Phe-Gabapentin (9g) Following Oral Administration to Rats The pharmacokinetics of the prodrug Cholyl-Phe-Gabapentin (9g) were examined in rats. Three groups of four male Sprague-Dawley rats (approx 200 g) with jugular cannulae each received one of the following treatments: A) a single bolus intravenous injection of Gabapentin (25 mg/kg, as a solution in water); B) a single oral dose of Gabapentin (25 mg/kg, as a solution in water) administered by oral gavage; C) a single oral dose of (9g) (103.5 mg/kg, as a solution in water) administered by oral gavage. Animals were fasted overnight prior to dosing and until 4 hours post-dosing. Serial blood samples were obtained over 24 hours following dosing and blood was processed for plasma by centrifugation. Plasma samples were stored at −80° C. until analyzed.

Concentrations of (9g) or (2) in plasma samples were determined by LC/MS/MS as described above. Plasma (50 µL) was precipitated by addition of 100 mL of methanol and supernatent was injected directly onto the LC/MS/MS system. Following oral administration of Gabapentin, concentrations of Gabapentin in plasma reached a maximum at 1.3±0.5 hours ($T_{max}$) and declined thereafter with a terminal half-life of 3.0±1.3 hours. The oral bioavailability of Gabapentin was 87±18%. Following oral administration of Cholyl-Phe-Gabapentin (9g), concentrations of Gabapentin in plasma reached a maximum at ~7.1 hours post-dosing and declined thereafter with a terminal half-life of~5.1 hours. Concentrations of released Gabapentin in plasma were sustained beyond 24 hours. These data indicate that prodrug Cholyl-Phe-Gabapentin (9g) is metabolized to Gabapentin (2) in vivo, and that a substantially sustained release of Gabapentin was achieved following oral administration of (9g) compared to the relatively rapid clearance observed for oral Gabapentin.

Example 7

Sustained Release of Gabapentin (2) from Cholyl-Gly-Gabapentin (9a) Following Oral Administration to Rats Following oral administration of Cholyl-Gly-Gabapentin (9a) (90.4 mg/kg, as a solution in water) according to the protocol of Example 6 above, concentrations of Gabapentin in plasma reached a maximum at~8.0 hours post-dosing and declined thereafter with a terminal half-life of~6.9 hours. Concentrations of released Gabapentin in plasma were sustained beyond 24 hours. These data indicate that prodrug Cholyl-Gly-Gabapentin (9a) is metabolized to Gabapentin (2) in vivo, and that a substantially sustained release of Gabapentin was achieved following oral administration of (9a) compared to the relatively rapid clearance observed for oral Gabapentin.

Example 8

Sustained Release of Gabapentin (2) from Cholyl-Tyr-Gabapentin (9h) Following Oral Administration to Rats Following oral administration of Cholyl-Tyr-Gabapentin (9h) (106 mg/kg, as a solution in water) according to the protocol of Example 6 above, concentrations of Gabapentin in plasma reached a maximum at ~7.3 hours post-dosing and declined thereafter with a terminal half-life of ~4.5 hours. Concentrations of released Gabapentin in plasma were sustained beyond 24 hours. These data indicate that prodrug Cholyl-Tyr-Gabapentin (9h) is metabolized to Gabapentin (2) in vivo, and that a substantially sustained release of Gabapentin was achieved following oral administration of (9h) compared to the relatively rapid clearance observed for oral Gabapentin.

In view of the above disclosure, it is understood, of course, that combinations of substituents within the compounds of the present invention do not include any combination that is chemically impossible or non-feasible as would be appreciated by one skilled in the art.

References

Arya, P.; Burton, G. W. Bile acids for biological and chemical applications and processes for the production thereof. U.S. Pat. No. 5,541,348, 1996.

Baringhaus, K. -H.; Matter, H.; Stengelin, S.; Kramer, W. Substrate specificity of the ileal and hepatic $Na^+$/bile acid cotransporters of the rabbit. II. A reliable 3D QSAR pharmacophore model for the ileal $Na^+$/bile acid cotransporter. *J. Lipid Res.* 1999, 40, 2158–2168.

Bryans, J. S.; Wustrow, D. J. 3-Substituted GABA analogs with central nervous system activity: a review. *Med. Res. Rev.* 1999, 19, 149–177.

Bundgaard, H. in *Design of Prodrugs* (Bundgaard, H. Ed.), Elsevier Science B. V., 1985, pp.1–92.

Ho, N. F. H. Utilizing bile acid carrier mechanisms to enhance liver and small intestine absorption. *Ann. N. Y. Acad. Sci.* 1987, 507, 315–329.

Jezyk, N.; Li, C.; Stewart, B. H.; Wu, X.; Bockbrader, H. N.; Fleisher, D. Transport of pregabalin in rat intestine and Caco-2 monolayers. *Pharm. Res.* 1999, 16, 519–526.

Kagedahl, M.; Swaan, P. W.; Redemann, C. T.; Tang, M.; Craik, C. S.; Szoka, F. C.; Oie, S. Use of the intestinal bile acid transporter for the uptake of cholic acid conjugates with HIV-1 protease inhibitory activity. *Pharm. Res.* 1997, 14, 176–180.

Kim, D. -C.; Harrison, A. W.; Ruwart, M. J.; Wilkinson, K. F.; Fisher, J. F.; Hidalgo, I. J.; Borchardt, R. T. Evaluation of bile acid transporter in enhancing intestinal permeability of renin-inhibitory peptides. *J. Drug Targeting* 1993, 1, 347–359.

Kramer, W.; Wess, G.; Schubert, G.; Bickel, M.; Girbig, F.; Gutjahr, U.; Kowalewski, S.; Baringhaus, K. -H.; Enhsen, A.; Glombik, H.; Mullner, S.; Neckermann, G.; Schulz, S.; Petzinger, E. Liver-specific drug targeting by coupling to bile acids. *J. Biol. Chem.* 1992, 267, 18598–18604.

Kramer, W.; Wess, G.; Neckermann, G.; Schubert, G.; Fink, J.; Girbig, F.; Gutjahr, U.; Kowalewski, S.; Baringhaus, K. -H.; Boger, G.; Enhsen, A.; Falk, E.; Friedrich, M.; Glombik, H.; Hoffmann, A.; Pittius, C.; Urmann, M. Intestinal absorption of peptides by coupling to bile acids. *J Biol. Chem.* 1994a, 269, 10621–10627.

Kramer, W.; Wess, G.; Enhsen, A.; Bock, K.; Falk, E.; Hoffmann, A.; Neckerman, G.; Gantz, D.; Schulz, S.; Nickau, L.; Petzinger, E.; Turley, S.; Dietschy, J. M. Bile acid derived HMG-CoA reductase inhibitors. *Biochim. Biophys. Acta* 1994b, 1227, 137–154.

Kramer, W.; Wess, G. Modified bile acid conjugates, and their use as pharmaceuticals. U.S. Pat. No. 5,462, 933, 1995.

Kramer, W.; Wess, G. Bile acid conjugates of proline hydroxylase inhibitors. U.S. Pat. No. 5,646,272, 1997a.

Kramer, W.; Wess, G. Bile acid derivatives, processes for their preparation, and use as pharmaceuticals. U.S. Pat. No. 5,668,126, 1997b.

Kramer, W.; Stengelin, S.; Baringhaus, K. -H.; Enhsen, A.; Heuer, H.; Becker, W.; Corsiero, D.; Girbig, F.; Noll, R.; Weyland, C. Substrate specificity of the ileal and hepatic Na+/ bile acid cotransporters of the rabbit. I. Transport studies with membrane vesicles and cell lines expressing the cloned transporters. *J Lipid Res.* 1999, 40, 1604–1617.

Kullak-Ublick, G. A.; Beuers, U.; Paumgartner, G. Hepatobiliary transport. *J. Hepatology* 2000, 32 (Suppl. 1), 3–18.

Mills, C. O.; Iqbal, S.; Elias, E. Ileal absorption of tyrosine-conjugated bile acids in Wistar rats. *Biochim. Biophys. Acta* 1987, 926, 154–159.

Navia, M. A.; Chaturvedi, P. R. Design principles for orally bioavailable drugs. *Drug Discovery Today* 1996, 1, 179–189.

Petzinger, E.; Nickau, L.; Horz, J. A.; Schulz, S.; Wess, G.; Enhsen, A.; Falk, E.; Baringhaus, K. -H.; Glombik, H.; Hoffmann, A.; Mullner, S.; Neckermann, G.; Kramer, W. Hepatobiliary transport of hepatic 3-hydroxy-3-methylglutaryl coenzyme A reductase inhibitors conjugated with bile acids. *Hepatology* 1995, 22, 1801–1811.

Reiner, A. Process for preparing ursodeoxycholic acid derivatives and their inorganic and organic salts having therapeutic activity. Eur. Patent 0 272 462 B1, 1992.

Swaan, P. W.; Szoka, F. C.; Oie, S. Use of the intestinal and hepatic bile acid transporters for drug delivery. *Adv. Drug Delivery Rev.* 1996, 20, 59–82.

Swaan, P. W.; Hillgren, K. M.; Szoka, F. C.; Oie, S. Enhanced transepithelial transport of peptides by conjugation to cholic acid. *Bioconj. Chem.* 1997, 8, 520–525.

Tsuji, A.; Tamai, I. Carrier-mediated intestinal transport of drugs. *Pharm. Res.* 1996, 13, 963–977.

Each of the above references is incorporated herein by reference in its entirety.

What is claimed is:

1. A compound of formula (I):

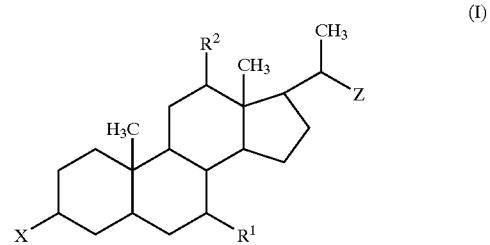

wherein:

$R^1$ and $R^2$ are independently hydrogen or hydroxy;

X is hydroxy;

Z is a group of formula -M-$Q^{x'}$, wherein M is —$CH_2CH_2C(O)$—, and wherein $Q^{x'}$ is of the following structure:

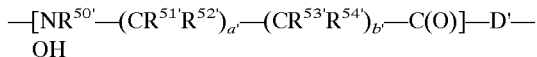

wherein a' and b' are independently 0 or 1, wherein at least one of a' and b' is 1;

$R^{50'}$ is hydrogen or $R^{50'}$ and $R^{51'}$ together with the atoms to which they are attached form a heterocyclyl ring;

$R^{51'}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{51'}$ and $R^{52'}$ together with the atoms to which they are attached form a cycloalkyl, substituted cycloalkyl, heterocyclyl or substituted heterocyclyl ring, or $R^{51'}$ and $R^{53'}$ together with the atoms to which they are attached form a cycloalkyl, substituted cycloalkyl, heterocyclyl or substituted heterocyclyl ring;

$R^{52'}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

$R^{53'}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{53'}$ and $R^{54'}$ together with the atoms to which they are attached form a cycloalkyl, substituted cycloalkyl, heterocyclyl or substituted heterocyclyl ring;

$R^{54'}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl; and D' is a pharmacologically active chemical compound containing at least one carboxylic acid group and at least one moiety selected from the group consisting of a primary amino group, a secondary amino group or a hydroxyl group;

with the provisos that D' is not a GABA analog; L-Dopa, an L-aromatic amino acid decarboxylase inhibitor, a catechol O-methyl transferase inhibitor or derivatives thereof; a naturally occuring α-amino acid or an ester or carboxamide of a naturally occuring α-amino acid; a polypeptide derived from a linear oligopeptide containing at least 3 α-amino acids; an oligonucleotide; a cyclophane derivative, a diethylenetriaminopentaacetate derivative, or paramagnetic ion chelates thereof; 5-de-O-methylsporaricin; a bis-(2-choroethyl)amino containing nitrogen mustard; an HMG-CoA reductase inhibitor; a proline hydroxylase inhibitor; or a steriod containing the carbon substructures of the following formulae;

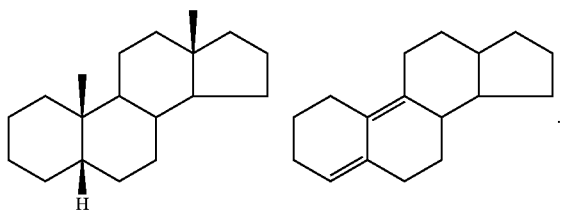

or a pharmaceutically acceptable salt thereof.

2. The compound according to claim 1, wherein $R^1$ and $R^2$ are both α-OH; $R^1$ is β-OH and $R^2$ is hydrogen; $R^1$ is α-OH and $R^2$ is hydrogen; $R^1$ is hydrogen and $R^2$ is α-OH; $R^1$ is β-OH and $R^2$ is α—OH; or $R^1$ and $R^2$ are both hydrogen.

3. The compound according to claim 1, wherein —[NR$^{50'}$—(CR$^{51'}$R$^{52'}$)$_{a'}$—C(O)]— is a moiety derived from a naturally occurring α-amino acid.

4. The compound according to claim 3, wherein b' is 0, and a' is 1.

5. A pharmaceutical composition comprising a pharmaceutically acceptable carrier and a compound according to claim 1.